US009056169B2

(12) United States Patent
Strickland et al.

(10) Patent No.: US 9,056,169 B2
(45) Date of Patent: Jun. 16, 2015

(54) COMMUNICATION PROTOCOL THAT SUPPORTS PASS-THRU COMMUNICATION

(71) Applicant: ROCHE DIAGNOSTICS OPERATIONS, INC., Indianapolis, IN (US)

(72) Inventors: Raymond Strickland, Indianapolis, IN (US); Kurt Klem, Indianapolis, IN (US); Mark Nierzwick, Brownsburg, IN (US)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 0 days.

(21) Appl. No.: 14/151,162

(22) Filed: Jan. 9, 2014

(65) Prior Publication Data
US 2014/0128804 A1    May 8, 2014

Related U.S. Application Data

(63) Continuation of application No. 12/976,313, filed on Dec. 22, 2010, now Pat. No. 8,672,874.

(51) Int. Cl.
*A61M 31/00*    (2006.01)
*H04W 76/02*    (2009.01)
(Continued)

(52) U.S. Cl.
CPC .......... *A61M 5/1723* (2013.01); *H04W 76/023* (2013.01); *G06F 19/3406* (2013.01)

(58) Field of Classification Search
CPC ............ A61M 5/1723; G06F 19/3406; H04W 76/023
USPC .............. 604/65–67, 131, 151; 370/464–468, 370/498, 503; 128/DIG. 12, DIG. 13
See application file for complete search history.

(56) References Cited

U.S. PATENT DOCUMENTS

| 6,424,847 B1 | 7/2002 | Mastrototaro et al. |
| 6,895,263 B2 | 5/2005 | Shin et al. |
| 6,931,327 B2 | 8/2005 | Goode, Jr. et al. |

(Continued)

FOREIGN PATENT DOCUMENTS

WO    WO-2008154467 A1    12/2008

OTHER PUBLICATIONS

Bluetooth SIG, "Bluetooth User Interface", www.bluetooth.org/Technical/Specifications/whitepapers.htm (Sep. 13, 2007).

(Continued)

*Primary Examiner* — Manuel Mendez
(74) *Attorney, Agent, or Firm* — Harness, Dickey

(57) ABSTRACT

A private extension of the IEEE 11073 standard for enabling pass-thru communication between a external computing device and a medical device via a diabetes management device is disclosed herein. Within this context, a diabetes management system for configured to allow pass thru communication is described. The system includes a diabetes management device in communication with a external computing device and the first medical device. A pass-thru module of the diabetes management device uses a set of pass-thru commands for establishing a pass-thru communication path and enabling communication between the external computing device and the first medical device, and wherein the set of pass-through commands is defined in compliance with a communication protocol defined in accordance with IEEE standard 11073-20601.

19 Claims, 11 Drawing Sheets

(51) Int. Cl.
  *A61M 5/172* (2006.01)
  *G06F 19/00* (2011.01)

(56) References Cited

U.S. PATENT DOCUMENTS

| | | |
|---|---|---|
| 7,003,341 B2 | 2/2006 | Say et al. |
| 7,029,444 B2 | 4/2006 | Shin et al. |
| 7,098,803 B2 | 8/2006 | Mann et al. |
| 7,190,988 B2 | 3/2007 | Say et al. |
| 7,276,029 B2 | 10/2007 | Goode, Jr. et al. |
| 7,599,726 B2 | 10/2009 | Goode, Jr. et al. |
| 7,797,028 B2 | 9/2010 | Goode, Jr. et al. |
| 7,826,382 B2 | 11/2010 | Sicurello et al. |
| 8,073,008 B2 | 12/2011 | Mehta et al. |
| 2002/0193670 A1 | 12/2002 | Garfield et al. |
| 2002/0193678 A1 | 12/2002 | Kruger |
| 2002/0193679 A1 | 12/2002 | Malave et al. |
| 2007/0055799 A1 | 3/2007 | Koehler et al. |
| 2007/0255125 A1 | 11/2007 | Moberg et al. |
| 2008/0097908 A1 | 4/2008 | Dicks et al. |
| 2008/0119708 A1 | 5/2008 | Budiman |
| 2008/0312512 A1 | 12/2008 | Brukalo et al. |
| 2008/0312584 A1 | 12/2008 | Montgomery et al. |
| 2008/0312585 A1 | 12/2008 | Brukalo et al. |
| 2009/0149803 A1 | 6/2009 | Estes et al. |
| 2009/0254037 A1 | 10/2009 | Bryant, Jr. et al. |
| 2010/0115279 A1 | 5/2010 | Frikart et al. |
| 2010/0305421 A1 | 12/2010 | Ow-Wing |
| 2012/0093311 A1 | 4/2012 | Nierzwick et al. |

OTHER PUBLICATIONS

Cagalj et al., "Key Agreement in Peer-to-Peer Wireless Networks", Proceedings of the IEEE, IEEE New York, US: vol. 94, No. 2 (Feb. 1, 2006).

Continua Design Guidelines 2010, Oct. 1, 2010.

Part 10417: Device Specialization-Glucose Meter, IEEE Std 11072-10417, May 8, 2009.

Part 20601; Application Profile—Optimized Exchange Protocol, IEEEStd 11073-20601, Sep. 26, 2008.

Sye Loong Keoh et al., "Securing Body Sensor Networks: Sensor Association and Key Management", Pervasive Computing and Communications (2009).

Xiao et al., "A Survey of Key Management Schemes in Wireless Sensor Networks", Computer Communications, Elsevier Science Publishers BV, Amsterdaym NL, vol. 30 Nos. 11-12 (Aug. 24, 2007).

COMMUNICATION PROTOCOL THAT SUPPORTS PASS-THRU COMMUNICATION

CROSS-REFERENCE TO RELATED APPLICATIONS

This application is a continuation of U.S. patent application Ser. No. 12/976,313 filed on Dec. 22, 2010, now U.S. Pat. No. 8,672,874. The entire disclosure of the above application is incorporated herein by reference.

FIELD

The present disclosure relates to a communication protocol for medical devices used for diabetes care and, more particularly, to a communication protocol that supports pass-thru communication between an external computing device and a medical device used in the treatment of diabetes via a diabetes management device.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex as the level of blood glucose entering the bloodstream is dynamic. Variation of insulin in the bloodstream that controls the transport of glucose out of the bloodstream also complicates diabetes management. Blood glucose levels are sensitive to diet and exercise, but also can be affected by sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is often highly intrusive because of the need to consistently obtain reliable diagnostic information, follow prescribed therapy, and manage lifestyle on a daily basis. Daily diagnostic information, such as blood glucose concentration, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data that are acquired from medical devices, personal healthcare devices, patient recorded information, healthcare professional tests results, prescribed medications and recorded information. Patients with diabetes and their healthcare professionals interact with a variety of medical devices and systems to help manage the disease. including performing structured collection procedures. For each of these differing types of medical devices, there is a need to aggregate, manipulate, manage, present, and communicate diagnostic data and prescriptive data from multiple data sources in an efficient manner to improve the care and health of a person with diabetes, so the person with diabetes can lead a full life and reduce the risk of complications from diabetes. There is also a need to aggregate, manipulate, manage, present, and communicate such diagnostic data and prescriptive data amongst the different types of medical devices using a standard communication protocol. IEEE 11073 is an exemplary communication standard that addresses interoperability and communication amongst medical devices such as blood pressure monitors, blood glucose monitors and the like. Within the context of such communication protocols, there is a further need to support advanced communication features, such as communications between devices not configured to directly communicate with one another.

The background description provided herein is for the purpose of generally presenting the context of the disclosure.

SUMMARY

In an aspect of the disclosure, a computer-implemented diabetes management system is provided. The diabetes management system is configured to allow pass thru communication. The diabetes management system includes a diabetes management device, an external computing device that communicates with the diabetes management device over a first bidirectional communications link. The diabetes management device and the external computing device exchange first data packets of a first data packet structure over the first bidirectional communication link. The diabetes management system further includes a first medical device that performs a task related to diabetes management and that communicates with the diabetes management device over a second bidirectional communications link; wherein the diabetes management device and the first medical device exchange second data packets of a second data packet structure over the second bidirectional communication link. The diabetes management device includes a pass-thru module that:
  i) selectively establishes a pass-thru communication path between the external computing device and the first medical device,
  ii) receives first data packets of the first data packet structure from the external computing device via the first bidirectional communications link,
  iii) converts the first data packets into second data packets of the second data packet structure, and iv) transmits the second data packets to the first medical device over the second bidirectional communications link;

The pass-thru module uses a set of pass-thru commands for establishing a pass-thru communication path and enabling communication between the external computing device and the first medical device, and wherein the set of pass-through commands is defined in compliance with a communication protocol defined in accordance with IEEE standard 11073-20601.

In another aspect of the disclosure, a diabetes management device configured to provide an efficient pass-thru communication path between a first medical device and an external computing device is disclosed. The diabetes management device includes a first communications module configured to establish a first bidirectional communications link with the external computing device. The diabetes management device and the external computing device exchange first data packets of a first data packet structure over the first bidirectional communication link. The diabetes management device further includes a second communications module configured to establish a second bidirectional communications link with the first medical device. The diabetes management device and the first medical device exchange second data packets of a second data packet structure over the second bidirectional communication link. The diabetes management device further comprises a pass-thru module that:

i) selectively establishes a pass-thru communication path between the external computing device and the first medical device,
ii) receives first data packets of the first data packet structure from the external computing device via the first bidirectional communications link,
iii) converts the first data packets into second data packets of the second data packet structure, and
iv) transmits the second data packets to the first medical device over the second bidirectional communications link;

The pass-thru module uses a set of pass-thru commands for establishing a pass-thru communication path and enabling communication between the external computing device and the first medical device, and wherein the set of pass-through commands is defined in compliance with a communication protocol defined in accordance with IEEE standard 11073-20601.

Further areas of applicability of the present disclosure will become apparent from the detailed description provided hereinafter. It should be understood that the detailed description and specific examples are intended for purposes of illustration only and are not intended to limit the scope of the disclosure.

Figure 1:
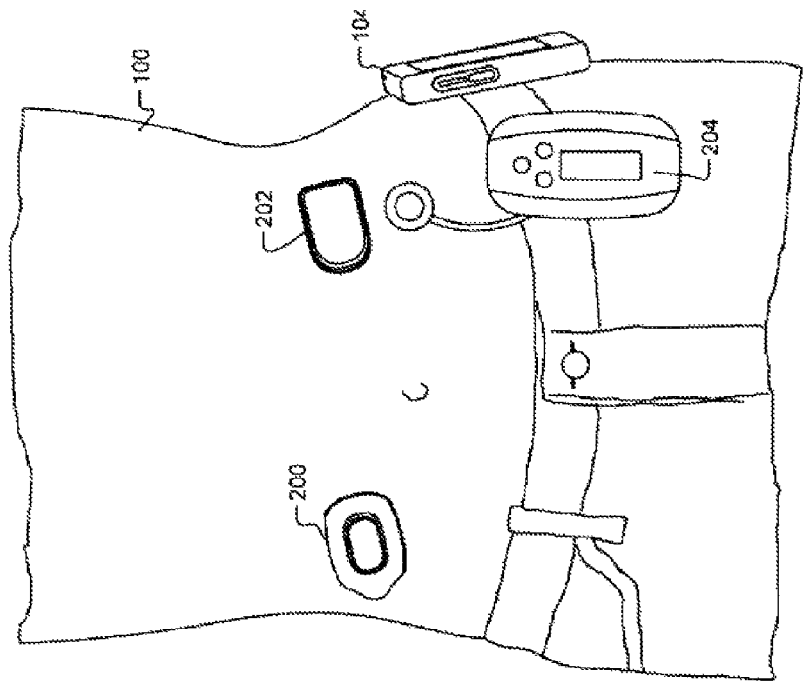
FIG. 1 is a diagram showing a patient and a treating clinician.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Referring to FIG. 1, a person 100 with diabetes and a healthcare professional 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
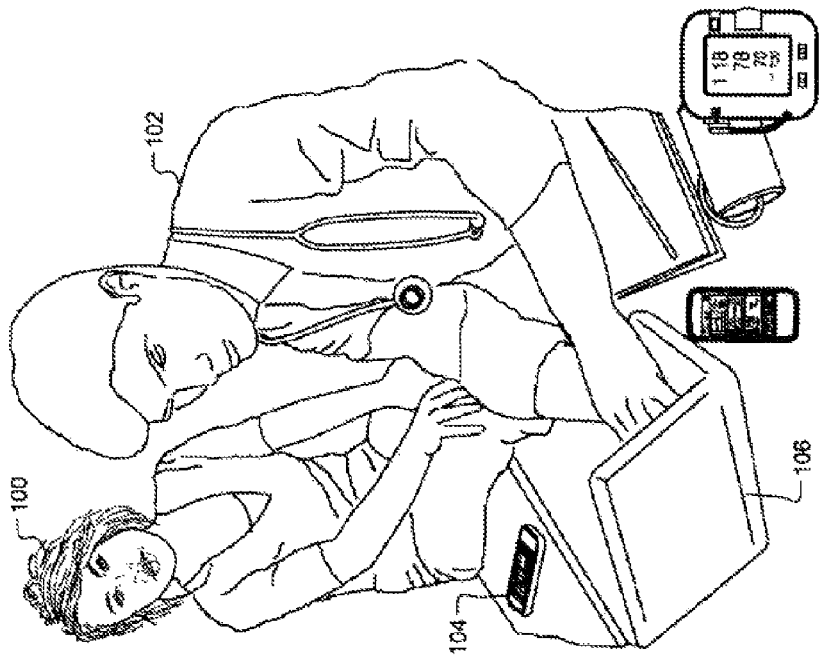
FIG. 2 is a diagram showing the patient with a continuous glucose monitor (CGM), an ambulatory durable insulin infusion pump, an ambulatory non-durable insulin infusion pump, and a diabetes manger.

Referring to FIG. 2, the patient 100 can use a continuous glucose monitor (CGM) 200, an ambulatory non-durable insulin infusion pump 202 or an ambulatory durable insulin infusion pump 204 (hereinafter insulin pump 202 or 204), and the handheld diabetes management device 104 (hereinafter the diabetes manager 104). The CGM 200 uses a subcutaneous sensor to sense and monitor the amount of glucose in the blood of the patient 100 and communicates corresponding readings to the diabetes manager 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives readings from the CGM 200 indicating insulin level in the blood of the patient 100.

The diabetes manager 104 transmits instructions to the insulin pump 202 or 204, which delivers insulin to the patient 100. Insulin can be delivered in a scheduled manner in the form of a basal dose, which maintains a predetermined insulin level in the blood of the patient 100. Additionally, insulin can be delivered in the form of a bolus dose, which raises the amount of insulin in the blood of the patient 100 by a predetermined amount.

Figure 3:
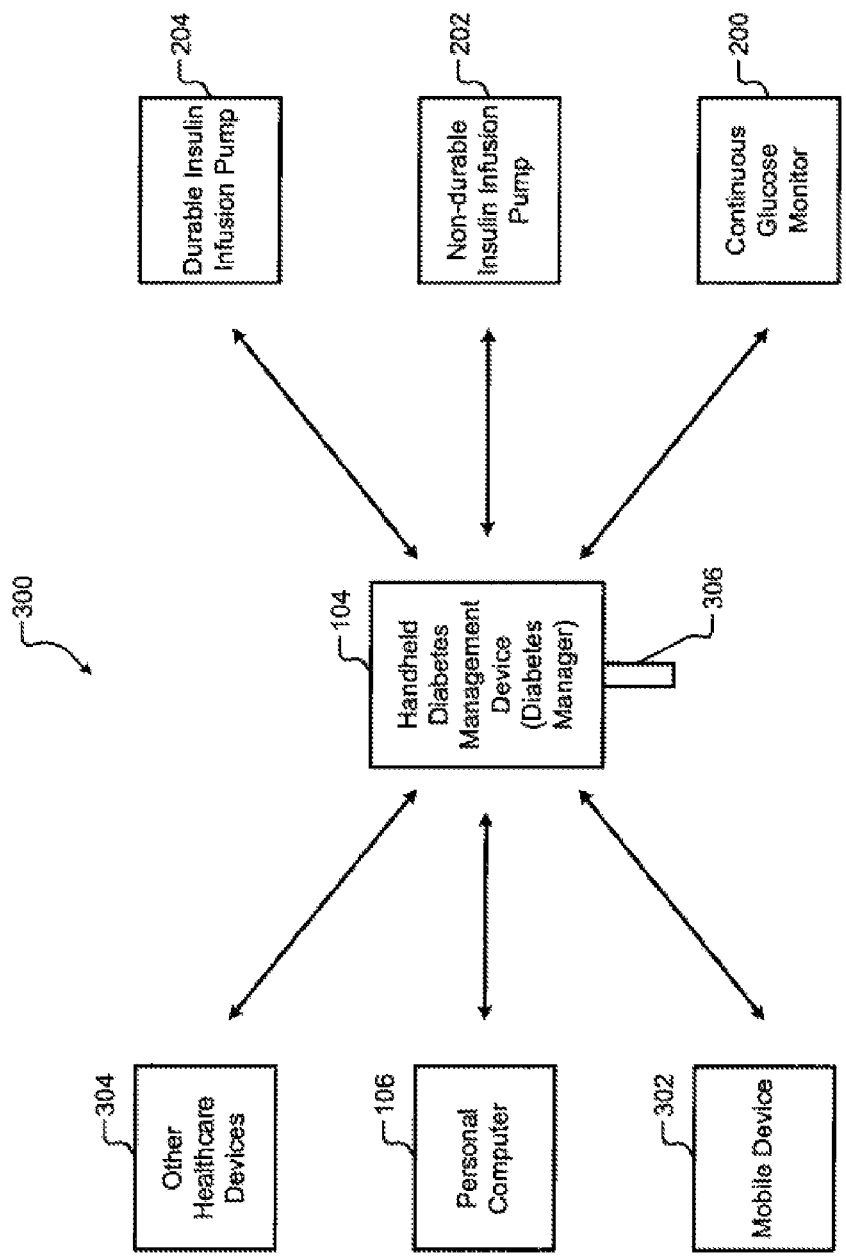
FIG. 3 is a block diagram showing an exemplary diabetes management system used by patients and clinicians to manage diabetes.

Referring to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the PC 106 with the diabetes analysis software, and other healthcare devices 304. The diabetes manager 104 is configured as a system hub and communicates with the devices of the diabetes management system 300. Alternatively, the insulin pump 204 or the mobile device 302 can serve as the system hub. Communication between the devices in the diabetes management system 300 can be performed using wireless interfaces (e.g., Bluetooth) and/or wired interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive blood glucose readings from one or more sources (e.g., from the CGM 200). The CGM 200 continuously measures the blood glucose level of the patient 100. The CGM 200 periodically communicates the blood glucose level to the diabetes manager 104. The diabetes manager 104 and the CGM 200 communicate wirelessly using a proprietary wireless protocol (e.g., Gazell wireless protocol developed by Nordic Semiconductor, Inc.).

Additionally, the diabetes manager 104 includes a blood glucose meter (BGM) and a port that communicates with the BGM (not shown). The port can receive a blood glucose measurement strip 306. The patient 100 deposits a sample of blood or other bodily fluid on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100. To facilitate collection of blood glucose measures, the diabetes manager 104 may executes one or more structured collection procedures as further described below.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the diabetes manager 104 can receive other information from the patient including meal and/or exercise schedules of the patient 100. The diabetes manager 104 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wired communication protocols can also be used.

In addition, the diabetes manager 104 can communicate with the other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 may use communication protocols compliant with ISO/IEEE 11073. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using USB, or other wired or wireless interfaces, such as Bluetooth. A diabetes management software running on the PC 106 includes a device management application and a diabetes management application. In some embodiments, the applications can be combined into an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a pager, or a personal digital assistant (PDA). The diabetes manager 104 can send data to an external network through the mobile device 302. The mobile device 302 can transmit messages to the external network upon receiving data from the diabetes manager 104.

Figure 4:
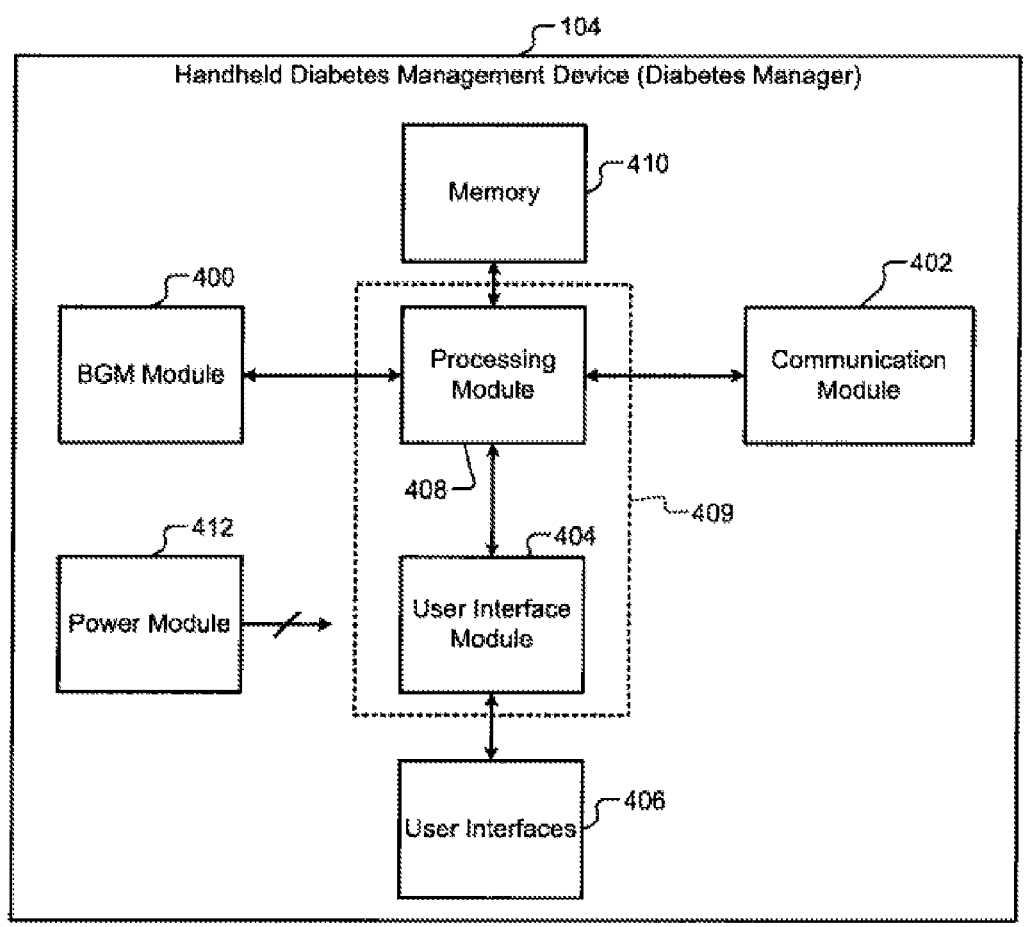
FIG. 4 is a functional block diagram of a diabetes manager.

An exemplary diabetes manager 104 is further described in relation to FIG. 4. The diabetes manager 104 comprises a blood glucose measuring (BGM) module 400, a first communication module 402, a second communication module 403, a user interface module 404, user interfaces 406, a processing module 408, memory 410, and a power module 412. The user interface module 404 and the processing module 408 can be implemented by an application processing module 409. The BGM module 400 includes a blood glucose measuring engine that analyzes samples provided by the patient 100 on the blood glucose measurement strip 306 and that measures the amount of blood glucose in the samples. The first communication module 402 can include multiple radios that communicate with different devices of the diabetes management system 300. The second communication module 403 can include ports for performing wired communication with external devices, e.g. an external computer. An exemplary port is a USB port. The user interface module 404 interfaces the diabetes manager 104 to various user interfaces 406 that the patient 100 can use to interact with the diabetes manager 104. For example, the user interfaces 406 can include keys, switches, a display, a speaker, a microphone, a secure digital (SD) card port, etc. (not shown).

The processing module 408 processes data received from the BGM module 400, the communication module 402, and the user interface module 404. The processing module 408 uses memory 410 for processing and storing data. The memory 410 can include volatile and nonvolatile memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 may include a rechargeable battery. The battery can be recharged using an adapter that plugs into a wall outlet. The battery can also be charged via the USB port of the diabetes manager 104.

For purposes of this disclosure, the diabetes manager 104 serves as a collection device. However, the collection device can be any portable electronic device that can provide an acquisition mechanism for determining and storing physiological measures of a person. For example, self-monitoring blood glucose meters and continuous glucose monitor devices are examples of collection devices used in diabetes care. While this disclosure makes reference to diabetes care, it is readily understood that the concepts disclosed herein can be applied to other types of chronic diseases and/or collection devices.

As evidenced by the list of devices which can be used to manage devices, it is beneficial to enable communication between the devices. In particular, a computer executing a diabetes management application and/or a device management application is configured to provide data, firmware, configuration files, instructions, or other communications to medical devices used in connection with the diabetes management of the patient and to retrieve data from the medical devices. As will be discussed in greater detail, however, medical devices such as an insulin pump or a CGM are typically only configured to communicate with the diabetes management device. While the computer may have capabilities to communicate with various devices, the pairing of such devices with any and all of a patient's devices can also be burdensome. Thus, to effectuate communication between the computer and the medical device, the diabetes management device is configured to support pass-thru communication. To enable pass-thru communication, the diabetes management device acts as a hub between an external computing device and medical device, e.g. an insulin pump or a CGM. The diabetes management device receives a data packet from one of the external computing device and the medical device and reconfigures and forwards the data packet to the other of the external computing device and the medical device.

Figure 5:
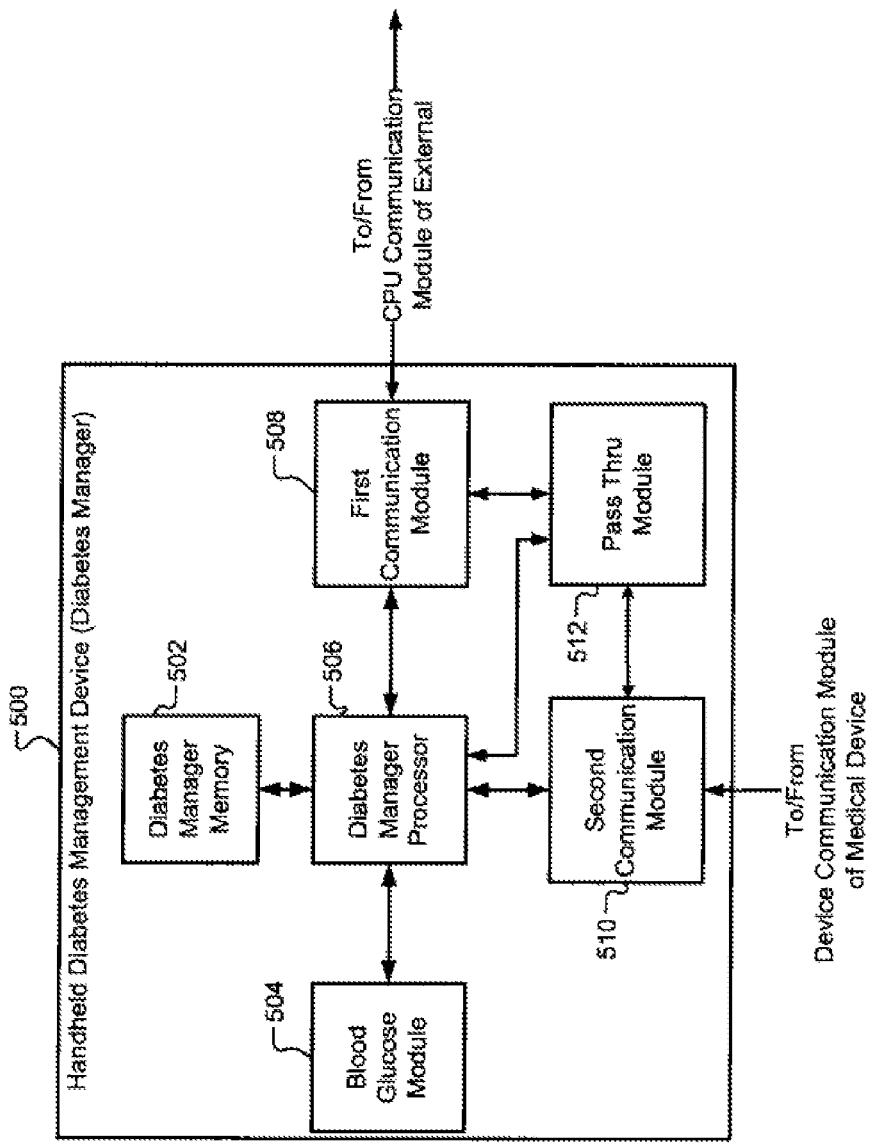
FIG. 5 is a block diagram showing an exemplary diabetes management device configured to effectuate pass-thru communication.
Figure 6:
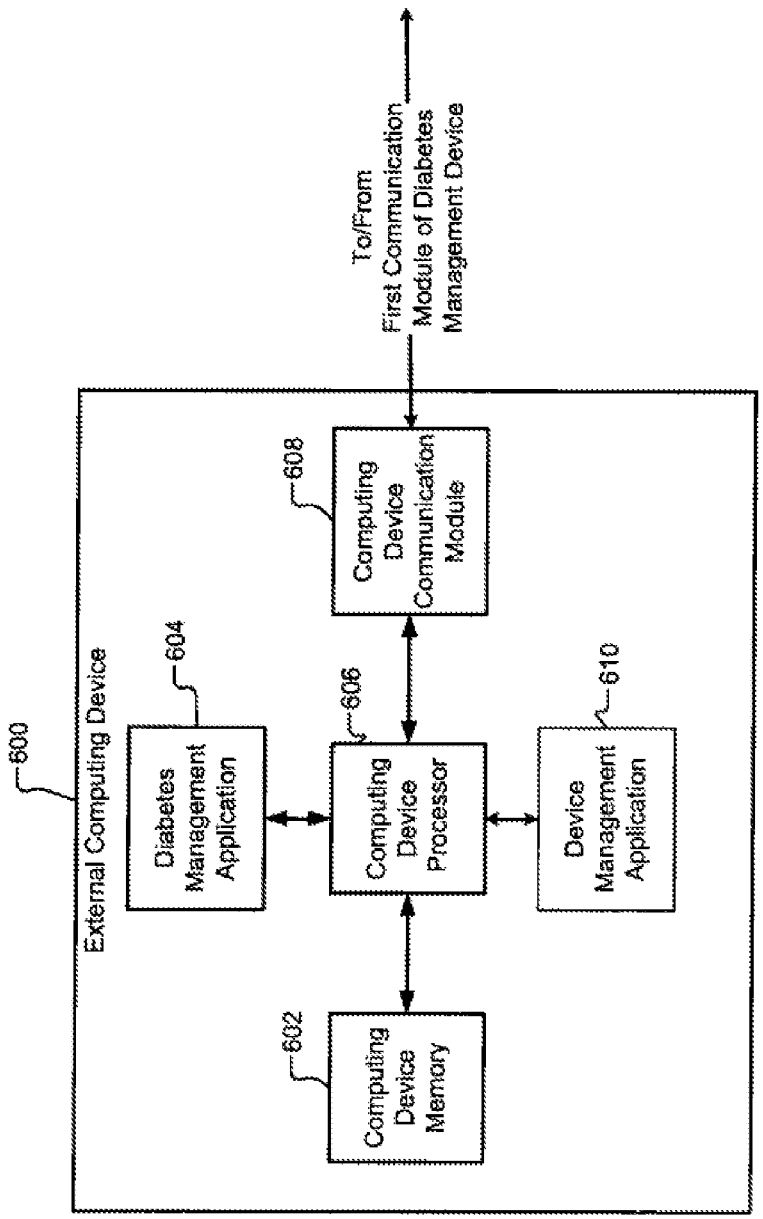
FIG. 6 is a block diagram showing an exemplary external computing device configured to communicate with an exemplary diabetes management device.
Figure 7:
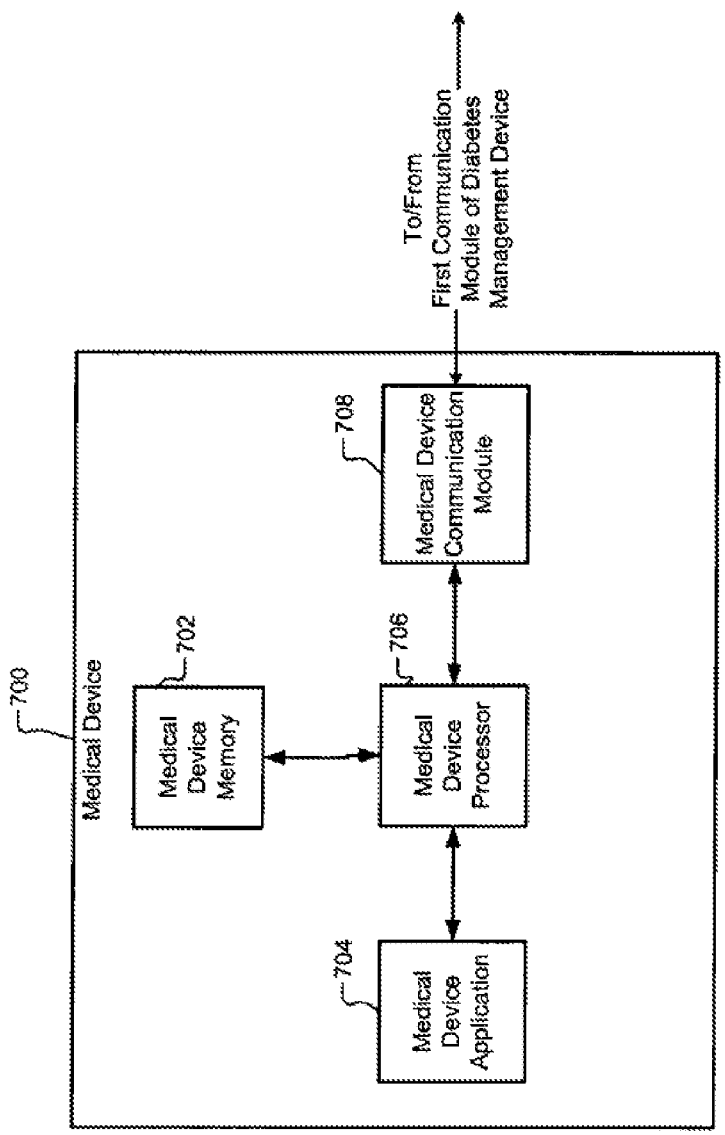
FIG. 7 is a block diagram showing an exemplary medical device configured to communicate with an exemplary diabetes management device.

FIGS. 5-7 illustrate exemplary embodiments of a diabetes management device 500, computing device 600, and a medical device 600, respectively, configured to perform pass-thru communication. In FIG. 5, a diabetes management device 500 ("diabetes manager") is depicted. As discussed with respect to FIG. 4, an exemplary diabetes manager 500 includes a diabetes manager processor 506, a diabetes manager memory 502, a blood glucose module 504, a first communication module 508, and a second communication module 510. The diabetes manager 500 depicted in FIG. 5 further includes a pass-thru module 512. The pass-thru module is configured to selectively establish a pass-thru communication path between the external computing device 600 and a medical device 700. It is noted that in some diabetes management systems, more than one medical device 700 may be in communication with diabetes manager 500. Thus, when pass-thru communication is enabled, the diabetes manager 500 may receive in a pass-thru command a designation of a particular medical device 700 to enable pass-thru communication with.

Referring now to FIG. 6, an exemplary external computing device 600 is depicted. The exemplary external computing device 600 includes a computing device processor 606, computing device memory 602, and at least one of a diabetes management application 604 and a device management application 610, either of which are embodied as computer executable instructions that can be stored on the computing device memory 602 and executed on the computing device processor 606. The exemplary diabetes management application 604 can collect and store data relating to a patient's diabetes and can generate instructions for managing the patient's diabetes, e.g. recommended insulin dosages or recommended food intake. It is appreciated that the diabetes management application 604 may perform additional tasks as well. The exemplary device management application 610 can perform device management tasks for the diabetes manager 500 and one or more medical devices 700. For instance, the device management application 610 can determine what version of firmware a particular device contains, and whether the firmware version is outdated and an upgrade is required. Further, the device management application 610 can download the firmware upgrade and transmit the firmware upgrade to the particular device. As can be appreciated, the external computing device 600 needs to communicate with the diabetes manager 500 so that the device management application 610 and the diabetes management application 604 can perform their respective functions. Thus, the external computing device utilizes a computing device communication module 608 to establish a bidirectional communication link with the diabetes manager 500. In an exemplary embodiment, the communication link is a wired communication link, e.g. a USB link between the external computing device 600 and the diabetes manager 500. It is appreciated that the external computing device 600 and the diabetes manager 500 exchange data packets having a predetermined structure via the bidirectional communication link. Furthermore, in other embodiments, it is appreciated that the bidirectional communication can be via a wireless link, e.g. WiFi, WiMax, Bluetooth, or the like.

Referring now to FIG. 7, a medical device 700 that performs a task related to diabetes management is depicted. An exemplary medical device 700 can be an insulin pump, a CGM, an insulin patch, or the like. The medical device 700 includes a medical device processor 706 and a medical device memory 702. The medical device 700 further includes a medical device application 704, which is embodied as computer readable instructions stored on the medical device memory 702 and executable by the medical device processor 706. The medical device application 704 is an application related to performing the task related to diabetes management. For instance, in the case of an insulin pump, the diabetes management application 704 can be an application for metering out particular amounts of insulin or for updating the firmware of the insulin pump. The medical device 700 further includes a medical device 700 communication module 708 for establishing a communication link with the diabetes manager 500. In an exemplary embodiment, the communication link in on which the medical device 700 communicates with the diabetes manager 500 is a wireless bidirectional communication link, e.g. Bluetooth, IR, Zigbee, Wifi, or the like. It is appreciated that the medical device 700 and the diabetes manager 500 exchange data packets having a predetermined structure via the bidirectional communication link.

Figure 8:
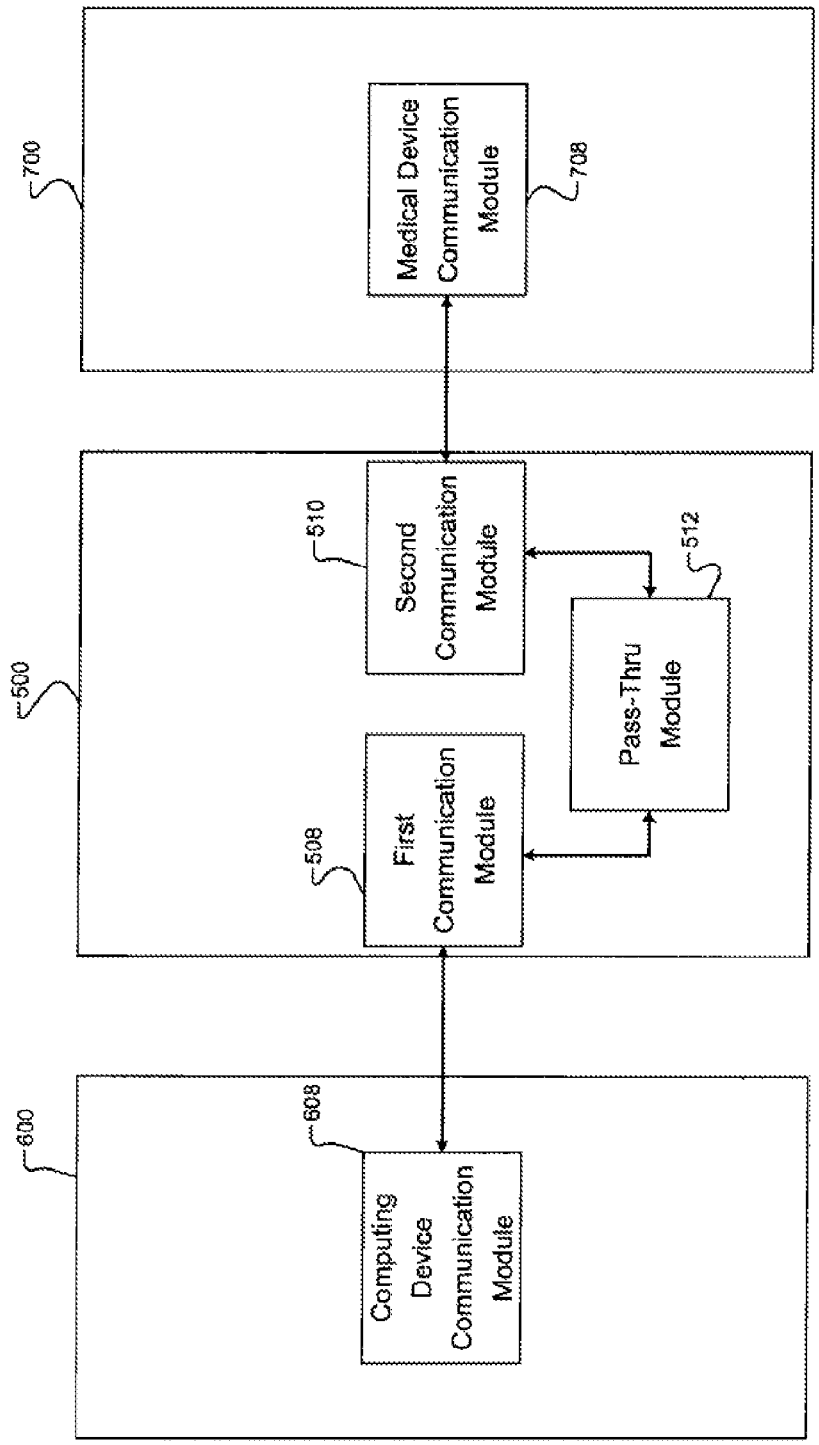
FIG. 8 is a block diagram showing an exemplary diabetes management system supporting pass-thru communication between an external computing device and a medical device.

FIG. 8 illustrates an example of a diabetes management system 800 having pass-thru communication enabled. As discussed, the diabetes manager 500 can be configured to communicate with an external computer 600 and one or more medical devices, e.g. an insulin pump, a CGM, an insulin patch or the like. The diabetes manager 500 communicates with the external computing device 600 via a first communication link between the first communication module 508 of the diabetes manager 500 and the computing device communication module 608 of the external computing device 600. The diabetes manager 500 communicates with the medical device 700 via a second communication link between the second communication module 510 of the diabetes manager 500 and the medical device communication module 708 of the medical device. An exemplary pass-thru module 512 is configured to receive, from the external computing device 600, a command which designates a particular medical device 700 to establish pass-thru communication with. As mentioned, the designated medical device 700 may be selected from a plurality of available medical devices. The pass-thru module 512 receives the command and establishes a pass-thru communication path between the particular medical device 700 and the external computing device 500.

Once the pass-thru communication path has been established, pass-thru communication may commence and data is transferred automatically between the external computing device 600 and the medical device 700. Pass-thru communication allows the external computing device 600 to transmit messages to the medical device 700 and the medical device 700 to transmit messages to the external computing device 600, despite no direct communication link exists between the two devices 600 and 700. To facilitate efficient communication between the external computing device 600 and the medical device 700, the pass-thru module 512 receives first data packets from the external computing device via the first bidirectional communications link. The first data packets may include a pass-thru command and a pass-thru payload data. The first data packets will have a structure that corresponds to the communication protocol used to transmit the data packet over the first bidirectional communications link. For example, a USB data packet may have a physical interface device (PID) followed by up to predetermined amount of bytes of payload data and a 16 bit cyclic redundancy check. The pass-thru module 512 converts the first data packets into second data packets. The second data packet includes the pass-thru payload data. The second data packet will have a structure that corresponds to the communication protocol used to transmit the second data packet over the second bidirectional communication link. For instance, an exemplary Bluetooth data packet may have an access code, followed by a header, followed by a payload having a predetermined length. Once the first data packet is converted into a second data packet, that is—a second data packet has been generated which contains the payload data of the first data packet, the pass-thru module transmits the second data packets to the medical device 700 over the second bidirectional communications link.

In response to successfully receiving the pass-thru payload data, the medical device 700 can confirm receipt to the diabetes management device 500, which in turn can confirm receipt to the external computing device 600.

Similarly, once the pass-thru communication path is established, the medical device 700 can transmit data to the external computing device 600 via the pass-thru communication path. The medical device 700 will transmit a third data packet of the second data packet structure to the second communication module 510 of the diabetes manager 500. The pass-thru module 512 will receive the third data packet, including a pass-thru command and a pass-thru payload, and convert the third into a fourth data packet of the first data packet structure including the pass-thru payload. The pass-thru module 512 will then transmit the fourth data packet to the external computing device 600 via the first communication link.

The pass-thru module 512 can also receive a disable pass-thru communication command to disable pass-thru communication. When a disable pass-thru communication command is received, the pass-thru module 512 will terminate the pass-thru communication path between the external computing device 600 and the medical device 700. Thus, once the pass-thru module is operating in a pass-thru mode, each time a command is received by the pass-thru module 512 the pass-thru module 512 will check the data packet to determine weather the command is a pass-thru command or a disable pass-thru communication command. If the command is of the former type, the pass-thru module 512 will convert the data packet into the appropriate data packet type and transmit the converted packet to the appropriate device. If, however, the command is a disable pass-thru command, the pass-thru module 512 will disable the pass-thru communication path.

By configuring the diabetes manager 500 to perform pass-thru communication, efficient communication can occur between the external computing device 600 and the medical device 700. For instance, if the firmware of an insulin pump or CGM needs to be updated, the device management application executing on the external computing device 600 can transmit an enable pass-thru communication command to the diabetes manager 500. Once a pass-thru communication path is established, the firmware update can be transmitted to the insulin pump via the pass-thru communication path. Similarly, if the diabetes management application requires data from a CGM or insulin pump, a request can be made to obtain data therefrom, and the data is transmitted to the external computing device 600 from the medical device 700 via the communication path. Furthermore, the pass-thru communication mode can allow a treating physician to configure a medical device 700 of a patient without actually pairing to the patient's medical device 700. Rather, configuration parameters can be transmitted to the medical device 700 from the external computing device 600 of the physician via the pass-thru communication path.

As discussed, the diabetes manager 500 is able to communicate with various devices. To facilitate efficient communications between the external computing device 600 or one or more medical devices 700, communications between devices are in compliance with ISO/IEEE 11073. ISO/IEEE 11073 is the medical and health device communication standard, which enables communication between medical devices and external computing devices. The ISO/IEEE 11073 standard provides for plug-and-play interoperability between medical devices and/or external computing devices. Further, the ISO/IEEE 11073 standard provides for efficient exchange of data collected at the point of care between devices. The result is that point-of-care data can retrieved, archived, and analyzed without the requirement of extensive software to support the exchange of data between devices. Furthermore, ISO/IEEE 11073-20601 defines a common framework for making an abstract model of personal health data available in transport-independent transfer syntax required to establish logical connections between systems and to provide presentation capabilities and services needed to perform communication tasks. The protocol is optimized to personal health usage requirements and leverages commonly used methods and tools wherever possible. In the case of blood glucose measures, the diabetes manager 500 may implement a device specialized communication protocol as defined by IEEE standard 11073-10417. For other types of measures, it is understood that the diabetes manager 500 may implement the applicable specialized communication protocol.

As discussed, ISO/IEEE 11073 standard enables communication amongst medical devices and other computer systems. By way of background, ISO/IEEE 11073 standard is based on an object oriented systems management paradigm. The overall system model is divided into three principal components: the domain information model (DIM), the service model, and the communication model. These three components work together to represent data, define data access and command methodologies and communicate the data from an agent to a manager. ISO/IEEE 11073-20601 may be referenced for a detailed description of the modeling constructs although each is described briefly below.

Figure 11:
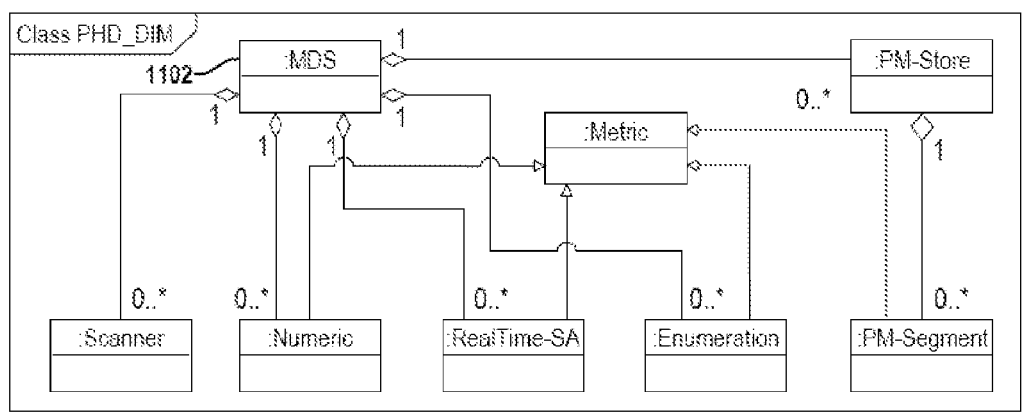
FIG. 11 is a class diagram for a personal health device defined in accordance with ISO/IEEE 11073-20601.

The domain information model is a hierarchical model that describes an agent as a set of objects. These objects and their attributes represent the elements that control behavior and report on the status of the agent and the data that an agent can communicate to a manager. With reference to FIG. 11, a class diagram for a personal health device is defined in accordance with ISO/IEEE 11073-20601. The Medical Device System (MDS) class 1102 is the root class of the device and contains attributes defining the device itself. Exemplary attributes include the type of device, i.e., glucose meter or insulin pump, manufacturer and model information and registered certification information. All other object classes are derived from the MDS class. For example, the Numeric class represents numeric measurements such as bG, carbohydrates, bolus amount, etc; whereas, the enumeration class represents status information and/or annotation information. For brevity purposes, a description is not provided for all of the classes shown in the figure.

Communication between the agent and the manager is defined by the application protocol in ISO/IEEE 11073-20601. The service model defines the conceptual mechanisms for the data exchange services. Object access services, such as Get, Set, Action and Event Reports, are mapped to messages that are exchanged between the agent and the manager. Protocol messages within the ISO/IEEE 11072 series of standards are defined in ASN.1. The messages defined in ISO/IEEE 11073-20601 can coexist with messages defined in other standard application profiles defined in the ISO/IEEE 11072 series of standards.

In general, the communication model supports the topology of one or more agents communicating over logical point-to-point connections to a single manager. More specifically, the communication model defines the construct of an application protocol data unit (APDU). ADPUs are data packets exchanged between agents and managers. For each logical point-to-point connection, the dynamic system behavior is defined by a connection state machine as specified in ISO/IEEE 11073-20601.

Two styles of configuration are defined in ISO/IEEE 11073-20601: standard and extended. Standard configurations are defined in the ISO/IEEE 11073-104zz specializations (such as the ISO/IEEE 11073-10417 Glucose Device specialization) and are assigned a well-known identifier (Dev-Configuration-Id). The usage of a standard configuration is negotiated at association time between the agent and the manager. If the manager acknowledges that it understands and wants to operate using the configuration, then the agent can begin sending measurements immediately. If the manager does not understand the configuration, the agent provides the configuration prior to transmitting measurement information.

In extended configurations, the agent's configuration is not predefined in a standard. The agent determines which objects, attributes, and values will be used in a configuration and assigns a configuration identifier. When the agent associates with a manager, it negotiates an acceptable configuration. Typically, the manager does not recognize the agent's configuration on the first connection, so the manager responds that the agent needs to send the configuration information as a configuration event report. If, however, the manager already understands the configuration, either because it was pre-loaded in some way or the agent had previously associated with the manager, then the manager responds that the configuration is known and no further configuration information needs to be sent.

Figure 9:
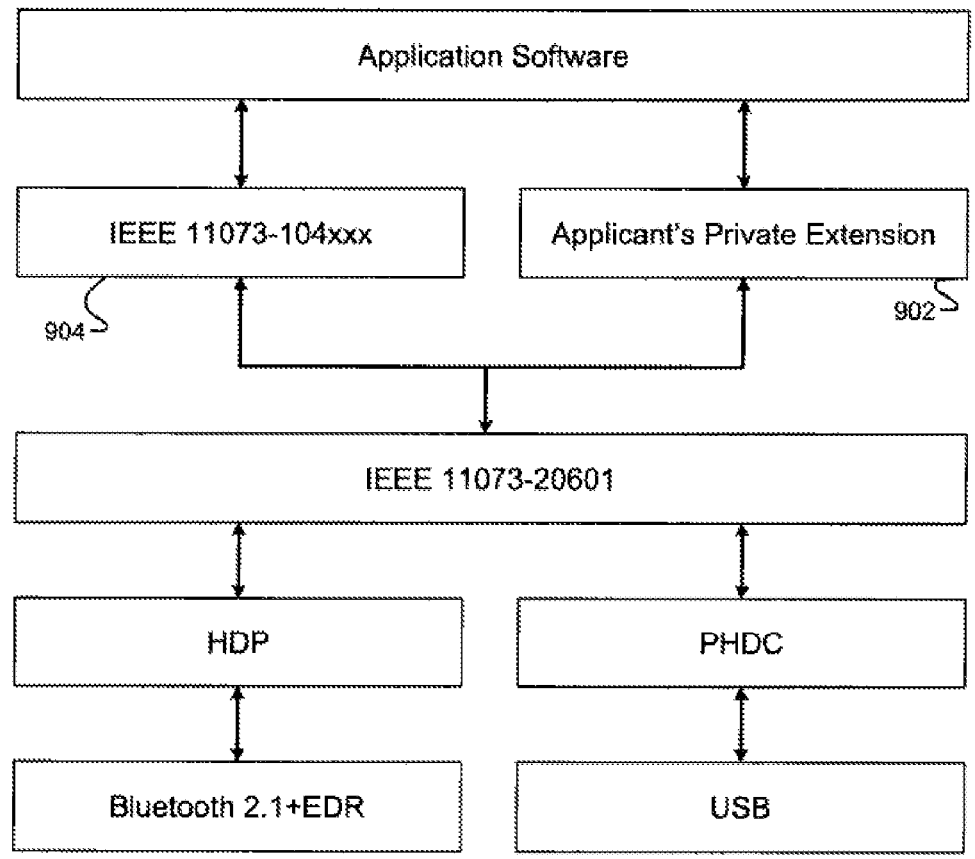
FIG. 9 is a block diagram depicting how applicant's private extension relates to the standardized communication protocols.

With reference to FIG. 9, this disclosure defines an extension 902 to these configurations, i.e., applicant's private extension, which is not published in any of the ISO/IEEE 11073-104xx device specializations 904. The relationship of Applicant's private extension 902 to the standardized communication protocols is shown in FIG. 9. Generally speaking, implementation of this private extension 902 defines the attributes and services to support the transfer and execution of specific commands and data. A basic framework for the private extension is first described below. Within this framework, a set of pass-thru commands for establishing a pass-thru communication path and enabling communication between an external computing device 600 and a medical device 700 are then presented by this disclosure. The set of command for pass-thru communication are used by the external computing device 600 and the medical device 700 to communication with one another despite no direct communication path there between. Further, as a result of the pass-thru communication, action such as updating firmware and file I/O can be preformed between the external computing device 600 and the medical device 700. Exemplary commands for firmware updating and file I/O are also disclosed herein. It is readily understood that other types of commands sets can also fall within the framework for the private extension.

In an exemplary embodiment of applicant's private extension, each agent device has one MDS object. This top-level MDS object is instantiated from the MDS class. The MDS object represents the identification and status of the agent through its attributes. Beyond the class definition provided by the IEEE standards, additional standardized classes may be supported by the agents and managers in accordance with applicant's private extension. The additional standardized classes are referred to herein as RPC classes. RPC private nomenclature codes are assigned from the manufacturer-specific range of private term codes (0xF000-0xFBFF) within the object oriented partition category (MDC_PART-OBJ). The partition number for object oriented classes and objects is 1.

The attributes for each RPC class are defined in tables that specify the name of the attribute, its value and its qualifier. The qualifiers mean M—attribute is mandatory, C—attribute is conditional and depends on the condition stated in the remark or value column, R—attribute is recommended, NR—attribute is not recommended, and O—attribute is optional. Mandatory attributes shall be implemented by an agent. Conditional attributes shall be implemented if the condition applies and may be implemented otherwise. Recommended attributes should be implemented by the agent. Not recommend attributes should not be implemented by the agent. Optional attributes may be implemented on an agent.

RPC classes that instantiate numeric type objects are created as they exist in the device. These numeric type objects represent additional result data that can be obtained from the device in the same manner they are obtained from the device specialization. These objects shall be added to the device attribute value map for authenticated managers. Attributes common across all of the RPC numeric objects are set forth in Appendix A. Furthermore, applicant's private extension has defined a few RPC numeric objects available to system designers Likewise, definitions for these common RPC numeric objects are set forth in Appendix A.

Applicant's private extension further defines an application protocol data unit as set forth below. An APDU represents the top-level message frame of the personal health device protocol. The extended APDU is added as an extension to the standard list of APDUs defined in the ISO/IEEE 11073-20601 specification.

```
Apdu Type ::=CHOICE {
aarq  [57856]  AarqApdu, -- Association Request [0xE200]
aare  [58112]  AareApdu, -- Association Response [0xE300]
rlrq  [58368]  RlrqApdu, -- Association Release Request [0xE400]
rlre  [58624]  RlreApdu, -- Association Release Response [0xE500]
abrt  [58880]  AbrtApdu, -- Association Abort [0xE600]
prst  [59136]  PrstApdu, -- Presentation APDU [0xE700]
prrp  [61440]  PrrpApdu - applicant's extended APDU [0xF000]}
```

A presentation APDU as defined in ISO/IEEE 11073-20601 is simply an octet string. Applicant's extended APDU adds a 16-bit CRC in order to ensure data integrity beyond the level provided by the transport and the ISO/IEEE 11073-20601 concept of reliable data channels. With this CRC, corrupted data can be detected by the application. This CRC covers the entire "RPC" part of the command invoke and command response APDUs.

```
PrrpApdup ::= SEQUENCE {
    data    OCTET STRING, (ENCODED VERSION OF
    DataApdu)
    crc     INT-U16 (checksum over the entire data field)
}
```

Applicant's extended APDU shall encapsulate unconfirmed Action Argument and confirmed Event Report Data APDUs defined by the ISO/IEEE 11073-20601 standard as follows:

```
ActionArgumentSimple ::= SEQUENCE {
    obj-handle      HANDLE
    action-type     OID-Type,   --From the nom-part-obj partition
                                --Subpartition ACT
                                (MDC_ACT_*)
    Action-info-args ANY DEFINED BY action-type
}
EventReportArgumentSimple ::=SEQUENCE {
    obj-handle      HANDLE
    event-time      Relative Time,
    event-type      OID-Type    --From the nom-part-obj partition
                                --Subpartition NOTI
                                (MDC_NOTI_*)
    event-info      ANY DEFINED BY event-type
}
```

The approach used to invoke applicant's defined commands is to extend the MDS object methods with applicant defined actions. The ISO/IEEE 11073-20601 unconfirmed action service uses the ActionArgumentSimple structure described above.

For the purposes of this specification, the fields would have the following values:

| | |
|---|---|
| handle | 0 (for the MDS object) |
| action-type | manufacturer specific code for applicant defined actions |
| action-info-args | manufacturer specific structure for each applicant defined action |

In order to invoke an applicant defined command, a manager would populate the action-type and action-info-arts of the ActionArgumentSimple object as follows:

| | |
|---|---|
| action-type | MDC_ACT_RPC_COMMAND_INVOKE |
| action-info-args | RpcCommandArguments |

The data objects used for command invocation action-info-args are defined as follows:

```
RpcCommandArguments ::= SEQUENCE {
    cmd-subcmd  INT-U16;    //Command/subcommand combined
    arguments   RpcDataArguments [ ];
}
RpcDataArguments ::= SEQUENCE {
    type    INT-U16;
    data    ANY DEFINED BY type
}
```

The encoding of ANY DEFINED BY is defined in ISO/IEEE 11073-20601 as follows: The ANY DEFINED BY type (ASN.1 1988/90) or the instance-of type (ASN.1 1994) is encoded by a header of a length field to specify the number of octets in the encoding of the selected value that follows. The length element shall be expressed as the number of bytes (octets) contained in the value element. An empty argument shall be indicated with the type element set to RPC_ARG_TYPE_EMPTY, the length element set to 2 and the value element set to zero as an INT-U16. An RpcCommandArguments structure which contains a cmd-subcmd value that requires no arguments will include a single RpcDataArguments element indicating an empty argument.

The approach used to return data as a result of an applicant defined command invocation is to extend the MDS event reports with applicant defined events. The ISO/IEEE 11073-20601 confirmed notification service uses the EventReportArgumentSimple structure previously discussed in this disclosure. For the purposes of the specification, the fields would have the following values:

| | |
|---|---|
| Handle | 0 (for the MDS object) |
| event-time | 0 (event time is not used for applicant actions) |
| event-type | manufacturer specific code for applicant defined command responses. - |
| event-info | manufacturer specific structure for each applicant defined response. |

In order to respond to an applicant defined command, an agent would populate the event-type and event-info of the EventReportArgumentSimple object as follows:

| | |
|---|---|
| Event-type | MDC_NOTI_RPC_COMMAND_RESPONSE |
| event-info | RpcDataArguments [ ] |

The RpcDataArguments object is the same as is defined for applicant defined actions.

Methods (actions) available for the MDS object are defined in the table below. These methods are invoked using the ACTION service. In the table, the Method/Action column defines the name of the method. The Mode column defines whether the method is invoked as an unconfirmed action (i.e., roiv-cmip-action) or a confirmed action (i.e., roiv-cmip-confirmed-action). The Action-type column defines the nomenclature ID to use in the action-type field of an action request and response. The action-info-args column defines the associated data structure to use in the action message for the action-info-args field of the request. The Resulting action-info-args column define the structure to use in the action-info-args of the response.

| Method/Action | Mode | Action-type | Action-info-args | Resulting action-info-args |
|---|---|---|---|---|
| RPC-Command-Invoke | Unconfirmed | MDC_ACT_RPC_COMMAND_INVOKE | RpcCommandArguments | n/a |

This method allows the manager to invoke an applicant defined system command.

Potential events sent by the RPC object are defined in the table below. A manager shall support all methods defined in the table.

| Method/Action | Mode | Event-type | Event-info Parameter | Event-reply-info |
|---|---|---|---|---|
| RPC-Data-Event | Confirmed | MDC_NOTI_RPC_COMMAND_RESPONSE | RpcDataArguments | RpcDataArguments |
| RPC-Error-Event | Confirmed | MDC_NOTI_RPC_ERROR_RESPONSE | RpcDataArguments | RpcDataArguments |

For the command response event, after the execution of an applicant defined command has been requested via the ACTION service, the agent will process the command, subcommand and parameter objects. If there are no command parameter errors, the result will be an agent-initiated event report reflecting the result of successful command processing. In the case of command success, the event report will contain a command-specific result string of data as defined by this specification.

For the error response event, after the execution of an applicant defined command has been requested via the ACTION service, the agent will process the command, subcommand and parameter objects. If there are parameter errors, the result will be an agent-initiated event report specifying the parameter error. If a manager receives an RPC_ERR_HARDWARE or RPC_ERR_APPLICATION response, the manager should invoke the RPC Read and Clear Status command to retrieve further error information available from the device.

Within this framework, a set of commands that support pass-thru communication is further described below. Communications with external devices connected to the device are accomplished by using the pass-thru mode command in conjunction with the subcommands discussed herein. In an exemplary embodiment, the command for performing pass-thru mode is RPC_CMD_PASS_THRU_MODE and has a value of 0x8700. The value of the pass-thru command can be "OR-ed" with one of the Firmware Upgrade subcommand values, discussed below, to form a complete command-subcommand value. As discussed, pass-thru mode communications can be used with only one device at a time. Thus, when a pass-thru mode is desired, an enable pass-thru mode command to enable pass-thru mode is issued. The enable pass-thru mode command instructs the diabetes manager 500 to enable pass-thru communications with the designated medical device 700. The input parameter is a component-id value which is obtained by first issuing a "Read External Device Information." The Read External Device Information command returns an error code indicating success (RPC_ERR_NO_ERRORS) or failure. If the designated medical device does not exist, the diabetes manager 50 returns an error message, e.g. RPC_ERR_APPLICATION_ERROR. An exemplary enable pass-thru command definition an a response thereto are defined as follows:

Command/Subcommand=0x8701
Input Parameters:

| Pass-Thru Device | PrivateOid (UINT16) |
|---|---|

Output Parameters:

| Error Code | Number |
|---|---|

RPC Command Invocation:

| cmd-subcmd | RPC_CMD_PASS_THRU_MODE \| RPC_SUBCMD_ENABLE_PASS_THRU_DEVICE |
|---|---|
| RpcDataArguments[0].type | RPC_ARG_TYPE_UINT16 |
| RpcDataArguments[0].length | 0x0002 |
| RpcDataArguments[0].value | Pass-Thru Device component-id value |

RPC Command Response:

| obj-handle | 0x0000 |
|---|---|
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 0x0002 |
| RpcDataArguments[0].value | Error code enumeration value |

Once an enable pass-thru command is issued, and the device manager 500 successfully enables pass-thru mode, i.e. establishing a pass-thru communication path between the external computing device 600 and the designated medical device 700, the external computing device 600 and the designated medical device 700 can communicate in pass-thru mode by issuing pass-thru commands. As discussed earlier, a pass-thru command instructs the diabetes manager 500 to transmit payload data to the currently pass-thru enabled medical device 700 or external computing device 600. The pass-thru command includes at least one input parameter. In an exemplary embodiment, the input parameter is the payload to be delivered to the pass-thru device 700 or 500 as an array of bytes, e.g. RPC_ARG_TYPE_UINT8_ARRAY. The pass-thru command returns an error code indicating successful transmission of the payload to the pass-thru device, e.g. RPC_ERR_NO_ERRORS, or failure, as shown in Appendix B. If there is no currently enabled pass-thru device, the device shall return an RPC_ERR_APPLICATION_ERROR. The following illustrates an exemplary definition of a pass-thru command and a response thereto:

Command/Subcommand=0x8703
Input Parameters:

| Tx Payload Data [ ] | UINT8 Array |
|---|---|

Output Parameters:

| Command Error Response (if the payload cannot be transmitted) | |
|---|---|
| Error Code | Number |
| Payload Data Event Report (if there are no errors to report) | |
| Rx Payload Data | UINT 8 array. |

RPC Command Invocation:

| | |
|---|---|
| cmd-subcmd | RPC_CMD_PASS_THRU_MODE \| RPC_SUBCMD_TRANSMIT_TO_DEVICE |
| RpcDataArguments[0].type | RPC_ARG_TYPE_UINT8_ARRAY |
| RpcDataArguments[0].length | Length of Tx Payload Data array in bytes |
| RpcDataArguments[0].value | Array of Tx Payload Data |

Upon receiving the command invocation, the diabetes manager 500 sends either a command error response event report or one or more Rx Payload Data event reports that contain payload data from the pass-thru device. The agent device will send the command error response if the Tx Payload Data cannot be sent to the pass-thru device. If there are no errors to report, the agent device shall start sending Rx Payload Data event reports as payloads are received from the pass-thru device. The following table illustrates exemplary command error responses:

RPC Command Error Response:

| | |
|---|---|
| obj-handle | 0x0000 |
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 0x0002 |
| RpcDataArguments[0].value | Error code enumeration value |

When pass-thru mode is enabled for communications with a pass-thru device, any transmission payloads received by the agent device shall be forwarded to the manager using an MDC_NOTI_RPC_PASSTHRU_DATA event report. The argument of the event report is the received payload data as an array of bytes (RPC_ARG_TYPE_UINT8_ARRAY). There is no manager response to this event report. The following is an exemplary table indicating a pass-thru event report:

RPC Pass-Thru Data Event Report:

| | |
|---|---|
| obj-handle | 0x0000 |
| event-time | 0xFFFFFFFF |
| event-type | MDC_NOTI_RPC_PASSTHRU_DATA |
| RpcDataArguments[0].type | RPC_ARG_TYPE_UINT8_ARRAY |
| RpcDataArguments[0].length | Length of Rx Payload Data array in bytes |
| RpcDataArguments[0].value | Array of Rx Payload Data |

When communication between the external computing device 600 and the designated medical device 700 is complete, one of the devices, usually the external computing device 600, will issue a disable pass-thru command indicating that the pass-thru communication path is to be disabled. The disable pass-thru command instructs the diabetes manager 500 to disable pass-thru communications with the currently enabled device. The command returns an error code indicating success (RPC_ERR_NO_ERRORS) or failure. See Appendix B for error code enumerations. If there is no currently enabled pass-thru device, the device shall return an RPC_ERR_APPLICATION_ERROR. An exemplary definition is a disable pass-thru command is defined as follows:

Command/Subcommand=0x8702

Input Parameters:
　None

Output Parameters:

| Error Code | Number |
|---|---|

RPC Command Invocation:

| | |
|---|---|
| cmd-subcmd | RPC_CMD_PASS_THRU_MODE \| RPC_SUBCMD_DISABLE_PASS_THRU_DEVICE |
| RpcDataArguments[0].type | RPC_ARG_TYPE_EMPTY |
| RpcDataArguments[0].length | 0x0002 |
| RpcDataArguments[0].value | 0x0000 |

RPC Command Response:

| | |
|---|---|
| obj-handle | 0x0000 |
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 0x0002 |
| RpcDataArguments[0].value | Error code enumeration value |

The foregoing illustrates an exemplary set of pass-thru commands for establishing a pass-thru communication path and enabling communication between the external computing device and the first medical device. It is noted that the set of pass-through commands is defined in compliance with a communication protocol defined in accordance with IEEE standard 11073-20601.

As discussed, when in pass-thru mode, the diabetes manager 500 can be used as a communication hub for performing such tasks as firmware upgrades. The set of commands for performing firmware upgrades is also defined with respect to IEEE standard 11073. Firmware upgrades are accomplished by using the Firmware Upgrade command in conjunction with the subcommands defined below. The exemplary command for performing Firmware Upgrade is RPC_CMD_FIRMWARE_UPGRADE and has a value of 0x8500. It must be "OR-ed" with one of the Firmware Upgrade subcommand values to form a complete command-subcommand value. It is recommended that the device be in Firmware Upgrade Mode before any file transfers related to the upgrade take place, so that the agent device can associate these files with the upgrade process.

Typically, before a firmware upgrade is performed on a medical device 700, the status of the firmware is read from the medical device 700. The status can be obtained from a medical device 700 by issuing a read firmware upgrade status command. The read firmware upgrade status command instructs the device to be updated to return a 16-bit unsigned integer (FwUpgradeStatus) that can contain bit flags which indicate the following status information:
　1. Firmware Upgrade feature status (upgrade-feature-enabled)
　2. Capable of Upgrade status (capable-of-upgrade)
　3. Upgrade in Progess status (upgrade-in-progress)
　4. Charging status (battery-is-charging)
　5. Device Busy status (device-is-busy)
The following is an exemplary definition of a read firmware upgrade status and a response thereto:
　Command/Subcommand=0x8501
　Input Parameters:
　　None Output Parameters:

| Upgrade Status Flags | FwUpgradeStatus |
|---|---|

RPC Command Invocation:

| cmd-subcmd | RPC_CMD_FIRMWARE_UPGRADE \| RPC_SUBCMD_FW_UPGRADE_STATUS |
|---|---|
| RpcDataArguments[0].type | RPC_ARG_TYPE_EMPTY |
| RpcDataArguments[0].length | 2 |
| RpcDataArguments[0].value | 0x0000 |

RPC Command Response:

| obj-handle | 0x0000 |
|---|---|
| event-time | 0xFFFFFFFF |
| event-type | MDC_NOTI_RPC_COMMAND_RESPONSE |
| RpcDataArguments[0].type | RPC_ARG_TYPE_UINT16 |
| RpcDataArguments[0].length | 2 |
| RpcDataArguments[0].value | FwUpgradeStatus value |

If the manager has not authenticated to the firmware upgrade role, the device returns an application error.

RPC Command Error Response

| obj-handle | 0x0000 |
|---|---|
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 2 |
| RpcDataArguments[0].value | Error code enumeration value |

Mapping of Firmware Upgrade Status to the FwUpgradeStatus Structure:

| Device Condition | FwUpgradeStatus Mnemonic |
|---|---|
| Device reports whether the firmware upgrade feature is enabled or disabled. (1 = enabled, 0 = not enabled) | upgrade-feature-enabled |
| Device reports whether it is currently capable of an upgrade (1 = capable, 0 = not capable) | capable-of-upgrade |
| Device reports whether a firmware upgrade is currently in progress (1 = in progress, 0 = not in progress. | upgrade-in-progress |
| Device reports whether or not the battery is currently charging (1 = charging, 0 = not charging) | battery-is-charging |
| Device reports whether or not it is busy with an internal operation or structured test protocol (1 = busy, 0 = not busy). | device-is-busy |

When the external computing device 600 or other device determines that the device to be upgraded requires a firmware upgrade, an enter firmware upgrade mode command is issued. The enter firmware upgrade mode command instructs the device to be upgraded to enter firmware upgrade mode. The command returns an error code indicating success, e.g. RPC_ERR_NO_ERRORS, or failure, e.g. RPC_ERR_APPLICATION_ERROR. It is noted that in the event of failure, the manager should check to see that the Firmware Upgrade feature is enabled in the device to be upgraded, using the "Read Firmware Upgrade Status" command discussed above. When the device to be upgraded receives this command and is not already in firmware upgrade mode, the device to be upgraded should perform preparatory tasks for the upgrade, which could include deleting files or terminating communications with external devices. In case the device to be upgraded is already in firmware upgrade mode the device should not re-initiate firmware upgrade mode, but instead simply return the RPC_ERR_NO_ERRORS response. An exemplary definition of an enter firmware upgrade mode command and a response thereto are defined as follows:

Command/Subcommand=0x8502

Input Parameters:
    None

Output Parameters:

| Error Code | Number |
|---|---|

RPC Command Invocation:

| cmd-subcmd | RPC_CMD_FIRMWARE_UPGRADE \| RPC_SUBCMD_ENTER_UPGRADE_MODE |
|---|---|
| RpcDataArguments[0].type | RPC_ARG_TYPE_EMPTY |
| RpcDataArguments[0].length | 2 |
| RpcDataArguments[0].value | 0 |

RPC Command Response:

| obj-handle | 0x0000 |
|---|---|
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 2 |
| RpcDataArguments[0].value | Error code enumeration value |

Once the device to be upgraded has entered upgrade mode, an apply firmware upgrade command is issued. The apply firmware upgrade command instructs the device to apply the firmware upgrade according to the procedures defined by the device specifications. The command returns an error code indicating success (RPC_ERR_NO_ERRORS) or RPC_ERR_APPLICATION_ERROR in the event of failure. In case the device to be upgraded is not in firmware upgrade mode, the device to be upgraded should return an application error response. The following is an exemplary definition of an apply firmware upgrade command and a response thereto:

Command/Subcommand=0x8504

Input Parameters:
    None

Output Parameters:

| Error Code | Number |
|---|---|

RPC Command Invocation:

| cmd-subcmd | RPC_CMD_FIRMWARE_UPGRADE \| RPC_SUBCMD_APPLY_FW_UPGRADE |
|---|---|
| RpcDataArguments[0].type | RPC_ARG_TYPE_EMPTY |
| RpcDataArguments[0].length | 2 |
| RpcDataArguments[0].value | 0 |

RPC Command Response:

| | |
|---|---|
| obj-handle | 0x0000 |
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 2 |
| RpcDataArguments[0].value | Error code enumeration value |

Once the firmware upgrade is complete, an exit firmware upgrade mode command is issued. The exit firmware upgrade command shall instruct the device to exit firmware upgrade mode. The command returns an error code indicating success (RPC_ERR_NO_ERRORS) or RPC_ERR_APPLICATION_ERROR in the event of failure. In case the device to be upgraded is not in firmware upgrade mode, the device should simply return the RPC_ERR_NO_ERRORS response. The following is an exemplary definition of an exit firmware upgrade mode command and a response thereto:

Command/Subcommand=0x8503
    Input Parameters:
      None
    Output Parameters:

| Error Code | Number |
|---|---|

RPC Command Invocation:

| | |
|---|---|
| cmd-subcmd | RPC_CMD_FIRMWARE_UPGRADE \| RPC_SUBCMD_EXIT_UPGRADE_MODE |
| RpcDataArguments[0].type | RPC_ARG_TYPE_EMPTY |
| RpcDataArguments[0].length | 2 |
| RpcDataArguments[0].value | 0 |

RPC Command Response:

| | |
|---|---|
| obj-handle | 0x0000 |
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 2 |
| RpcDataArguments[0].value | Error code enumeration value |

Further, the computing device 600 includes a set of file input/output ("file I/O") commands defined in accordance with the communication protocol defined in accordance with the ICC-11073 standard. These commands are directed to performing operations relating to the file system of the diabetes management system 500. Exemplary commands include commands to read a file, write to a file, to abort read or write operations, and to read a file directory.

An exemplary command for performing file I/O is RPC_CMD_FILE_IO and has a exemplary value of 0x8200. The exemplary command is "OR-ed" with one of the file I/O subcommand values to form a complete command-subcommand value. Exemplary commands and their respective subcommand values are discussed in greater detail below.

As a threshold matter, in an exemplary embodiment files transferred from a manager to an agent can be digitally signed. The digital signature can be generated in any known manner consistent with the IEEE-11073 standard. The levels of security associated with different file types will be specified by the digital signatures.

The following discusses exemplary subcommands within the realm of file I/O. It is appreciated that in the following subcommands, the filename parameter may include volume name and path name information in addition to the actual name of the file.

A first file I/O command is a read file command, which instructs a device to return contents of the specified file in the command as one or more File Data event reports. In an exemplary embodiment, the File Data event reports deliver the contents of the file sequentially. It is appreciated that in other embodiments, the contents of the file may be delivered to the requesting device non-sequentially. The size of successive File Data event report APDUs is equal to the value returned by the RPC_CMD_OPERATIONAL_INFO|RPC_SUBCMD_MAX_APDU_SIZE command except for the last event report APDU, which will have a length that is less than or equal to the Maximum APDU Size value. The following is an example of the read file command and a response thereto. Note that the value of the command/subcommand is the ORed value of the file I/O command and the read file subcommand value.

Command/Subcommand=0x8201
    Input Parameters:

| Filename | String |
|---|---|

Output Parameters:

| | |
|---|---|
| Command Error Response (if file does not exist or is corrupt) | |
|   Error Code | Number |
| File Data Event Reports (if there are no errors to report) | |
|   File Data | UINT 8 array. |

RPC Command Invocation:

| | |
|---|---|
| cmd-subcmd | RPC_CMD_FILE_IO \| RPC_SUBCMD_READ_FILE |
| RpcDataArguments[0].type | RPC_ARG_TYPE_STRING |
| RpcDataArguments[0].length | Length of the filename string |
| RpcDataArguments[0].value | String containing the filename. |

Upon receiving the command invocation, the device receiving the command transmits either a command error response event report or one or more file data event reports. The device receiving the command will send the command error response if the file does not exist on the device or if the contents of the file are corrupt. If there are no errors to report, the device sends file data event reports to the requesting device. In the case where the amount of file data is larger than can be transmitted with a single APDU (i.e. larger than the Maximum APDU Size), the device will send successive event reports of Maximum APDU Size until the file data is exhausted. The last event report containing file data can be indicated by sending an event report with a length that is less than the Maximum APDU Size or an event report containing a zero length file data entry.

RPC Command Error Response:

| | |
|---|---|
| obj-handle | 0x0000 |
| event-time | 0xFFFFFFFF |
| event-type | MDC_NOTI_RPC_ERROR_RESPONSE |

| | |
|---|---|
| RpcDataArguments[0].type | RPC_ARG_TYPE_UINT16 |
| RpcDataArguments[0].length | 2 |
| RpcDataArguments[0].value | Error code enumeration value |

RPC File Data Event Report:

| | |
|---|---|
| obj-handle | 0x0000 |
| event-time | 0xFFFFFFFF |
| event-type | MDC_NOTI_RPC_FILE_DATA |
| RpcDataArguments[0].type | RPC_ARG_TYPE_UINT8_ARRAY |
| RpcDataArguments[0].length | Length of file data array in bytes |
| RpcDataArguments[0].value | Array of file data |

The manager can be configured to instruct the device to abort the file transfer at any time by sending a Read File Abort command to the device. In this event the device can abort transfer of file data and send a File Transfer Abort response to the manager. If errors occur during the execution of this command, the manager shall discard all file data received (if any).

A second exemplary file I/O command is the write file data command. The write file data command instructs a device being written to receive contents of a specified file as one or more File Data event reports. In an exemplary embodiment, the File Data event delivers the contents of the file sequentially. It is appreciated that in other embodiments, the File Data event may also deliver the contents of the file non-sequentially. The size of successive File Data event report APDUs is equal to the value returned by the RPC_CMD_OPERATIONAL_INFO|RPC_SUBCMD_MAX_APDU_SIZE command. It is noted, however, the last event report APDU, which can be a length that is less than the Maximum APDU Size value. The following provides a definition of an exemplary write file data command and a response thereto:

Command/Subcommand=0x8202
Input Parameters:

| | |
|---|---|
| Filename | String |
| Write Mode | Number (New or Append) |

Output Parameters:

| | |
|---|---|
| Error Code | Number |

RPC Command Invocation:

| | |
|---|---|
| cmd-subcmd | RPC_CMD_FILE_IO \| RPC_SUBCMD_WRITE_FILE |
| RpcDataArguments[0].type | RPC_ARG_TYPE_STRING |
| RpcDataArguments[0].length | Length of the filename string |
| RpcDataArguments[0].value | String containing the filename. |
| RpcDataArguments[1].type | RPC_ARG_TYPE_UINT16 |
| RpcDataArguments[1].length | 2 |
| RpcDataArguments[1].value | Write Mode enumeration value |

RPC File Data Event Report:

| | |
|---|---|
| obj-handle | 0x0000 |
| event-time | 0xFFFFFFFF |
| event-type | MDC_NOTI_RPC_FILE_DATA |
| RpcDataArguments[0].type | RPC_ARG_TYPE_UINT8_ARRAY |
| RpcDataArguments[0].length | Length of file data array in bytes |
| RpcDataArguments[0].value | Array of file data |

RPC Command Error Response:

| | |
|---|---|
| obj-handle | 0x0000 |
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 2 |
| RpcDataArguments[0].value | Error code enumeration value |

Upon receiving the command invocation, the device being written to sends an error response event report to the manager. An RPC_ERR_APPLICATION_ERROR response indicates that the write file operation is not possible for one of the following reasons: Either the Write Mode was "New" and the file already exists on the device; or the Write Mode is "Append" and the file does not exist on the device.

An RPC_ERR_INVALID_PARAMETERS response indicates that the filename is invalid or the Write Mode is not a legal enumeration value. An RPC_ERR_HARDWARE response indicates that the volume is full.

An error response of RPC_ERR_NO_ERRORS triggers the manager to send one or more file data event reports. In the case where the amount of file data is larger than can be transmitted with a single APDU (i.e. larger than the Maximum APDU Size), the manager shall send successive event reports of Maximum APDU Size until the file data is exhausted. The last event report containing file data shall be indicated by sending an event report with a length that is less than the Maximum APDU Size or an event report containing a zero length file data entry.

Upon receiving the last file data event report, the device being written to verifies the file integrity by analyzing the digital signature contained within the file data. If the file integrity check fails, the device being written to sends an RPC_ERR_SECURITY_ERROR response to the manager.

If the file integrity check passes, the device being written to writes the file to the location specified by the path. If the device encounters an error in the process of writing the file data to the specified location, the device sends an RPC_ERR_HARDWARE response to the manager. If the device successfully writes the file data to the specified location, the device sends an RPC_ERR_NO_ERRORS response to the manager. If errors occur during the execution of this command, the device shall discard all file data received (if any).

As will be discussed below, that the device may instruct the manager to abort the file transfer at any time by sending a Write File Abort event report to the manager. In this event the manager can immediately abort transfer of file data.

As mentioned, the set of commands includes a read file abort command. The read file abort command instructs a device receiving a read file command to abort the transfer of file data started by read file command. The command returns an error code indicating success (RPC_ERR_NO_ERRORS) or RPC_ERR_APPLICATION_ERROR in the event of failure. The following provides an exemplary definition of the read file command and a response thereto:

Command/Subcommand=0x8203
Input Parameters:
None

Output Parameters:

| Error Code | Number |
|---|---|

RPC Command Invocation:

| | |
|---|---|
| cmd-subcmd | RPC_CMD_FILE_IO \| RPC_SUBCMD_READ_FILE_ABORT |
| RpcDataArguments[0].type | RPC_ARG_TYPE_EMPTY |
| RpcDataArguments[0].length | 2 |
| RpcDataArguments[0].value | 0 |

RPC Command Response:

| | |
|---|---|
| obj-handle | 0x0000 |
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 2 |
| RpcDataArguments[0].value | Error code enumeration value |

As mentioned, a device that received the write file command can generate and transmit a write file abort event report. The write file abort event report has a structure similar to a command but is not necessarily a command, as the write file abort event report does not trigger a response by the manager that issued the write file command. Rather, the write file abort event report instructs the manager to abort the transfer of write file data. It is noted that in some embodiments, the device issuing the write file abort event report may also specify an error code value to indicate the cause of the Write File Abort, which could be RPC_ERR_APPLICATION_ERROR or RPC_ERR_HARDWARE (indicating that the volume is full). The following defines an exemplary definition of a write file abort event report:

RPC Write File Abort Event Report:

| | |
|---|---|
| obj-handle | 0x0000 |
| event-time | 0xFFFFFFFF |
| event-type | MDC_NOTI_RPC_WRITE_FILE_ABORT |
| RpcDataArguments[0].type | RPC_ARG_TYPE_UINT16 |
| RpcDataArguments[0].length | 2 |
| RpcDataArguments[0].value | Error code enumeration value |

The set of file I/O commands further includes a delete file command. The delete file command is issued by the manager and instructs the device receiving the command to delete the specified file. In response to the command, the device returns an error code indicating success, e.g. RPC_ERR_NO_ERRORS, or one of the following error codes in the event of failure: RPC_ERR_INVALID_PARAMETERS if the file does not exist on the device; or RPC_ERR_APPLICATION_ERROR if the file is protected by the device and cannot be deleted. The following defines an exemplary definition of a delete file command and a response thereto:
Command/Subcommand=0x8204
Input Parameters:

| Filename | String |
|---|---|

Output Parameters:

| Error Code | Number |
|---|---|

RPC Command Invocation:

| | |
|---|---|
| cmd-subcmd | RPC_CMD_FILE_IO \| RPC_SUBCMD_DELETE_FILE |
| RpcDataArguments[0].type | RPC_ARG_TYPE_STRING |
| RpcDataArguments[0].length | Length of the filename string |
| RpcDataArguments[0].value | String containing the filename. |

RPC Command Response:

| | |
|---|---|
| obj-handle | 0x0000 |
| event-time | 0xFFFFFFFF |
| event-type | MDC_NOTI_RPC_ERROR_RESPONSE |
| RpcDataArguments[0].type | RPC_ARG_TYPE_UINT16 |
| RpcDataArguments[0].length | 2 |
| RpcDataArguments[0].value | Error code enumeration value |

The set of command can also include a read file directory command. The read file directory command instructs the device receiving the command to return a file/folder list of character strings, each of which specifies one file/folder entry in the file listing of the specified path. The device will send a command error response if the path does not exist on the device, e.g. RPC_ERR_INVALID_PARAMETERS, or if the contents of the path are corrupt, e.g. RPC_ERR_APPLICATION. The format of the pathname and the file list entries depends on the file system implementation of the device receiving the request. The file list does not include the contents of any subdirectories which exist within the folder of the specified path. The following defines an exemplary definition of a read file directory command and a response thereto:
Command/Subcommand=0x8205
Input Parameters:

| Pathname | String |
|---|---|

Output Parameters:

| Filelist Array [ ] | String |
|---|---|

RPC Command Invocation:

| | |
|---|---|
| cmd-subcmd | RPC_CMD_FILE_IO \| RPC_SUBCMD_FILE_DIRECTORY |
| RpcDataArguments[0].type | RPC_ARG_TYPE_STRING |
| RpcDataArguments[0].length | Length of the pathname string |
| RpcDataArguments[0].value | String containing the pathname. |

RPC Command Response:

| | |
|---|---|
| obj-handle | 0x0000 |
| event-time | 0xFFFFFFFF |
| event-type | MDC_NOTI_RPC_COMMAND_RESPONSE |
| RpcDataArguments[0].type | RPC_ARG_TYPE_STRING |
| RpcDataArguments[0].length | Length of Filelist Entry string in bytes |
| RpcDataArguments[0].value | Filelist Entry value |

-continued

| | |
|---|---|
| o | o |
| o | o |
| o | o |
| RpcDataArguments[n].type | RPC_ARG_TYPE_STRING |
| RpcDataArguments[n].length | Length of Filelist Entry string in bytes |
| RpcDataArguments[n].value | Filelist Entry value |

It is appreciated that the foregoing command definitions, response definitions, command and subcommand values are exemplary. Other definitions and values are contemplated and are within the scope of this disclosure.

Figure 10A:
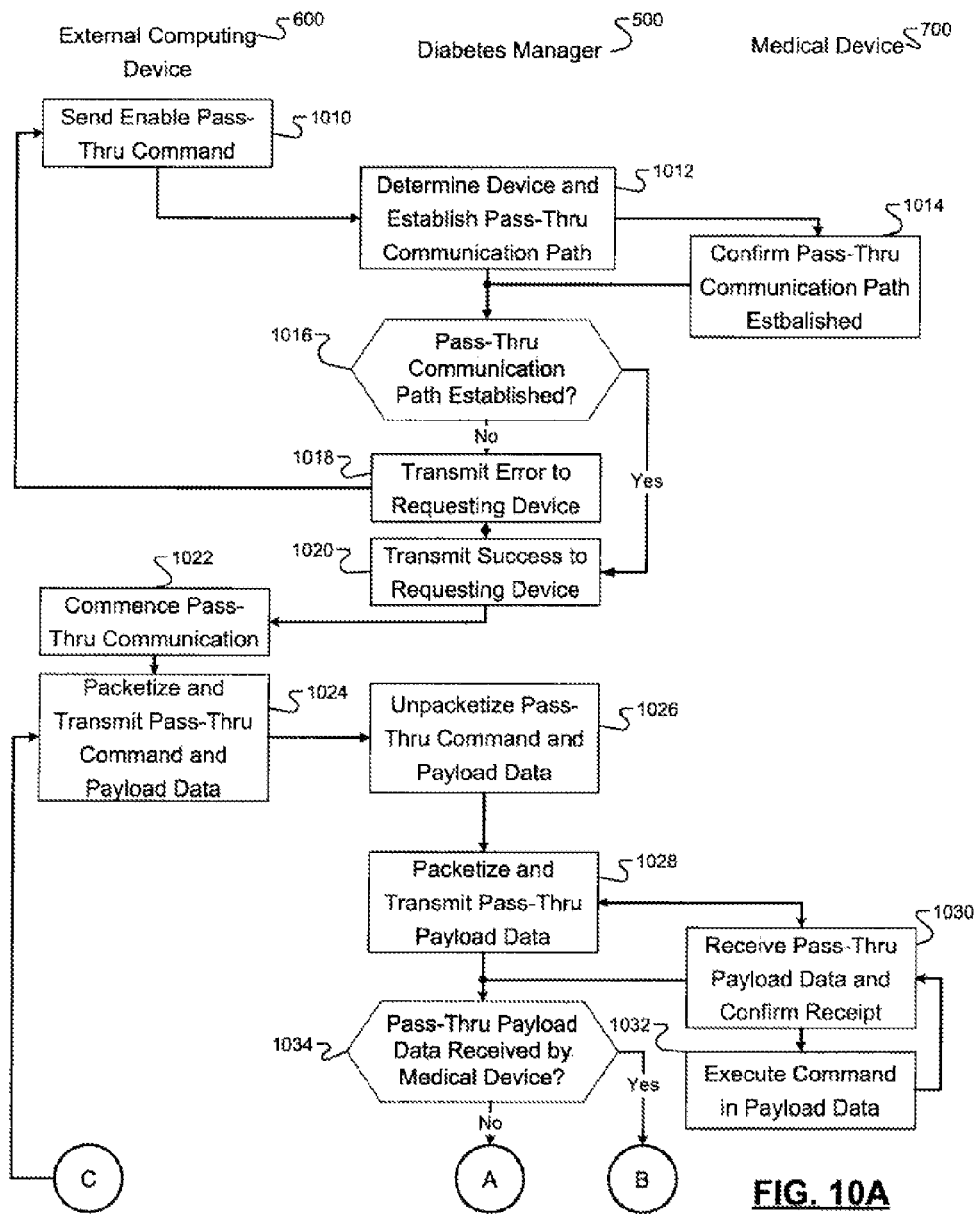
FIGS. 10A and 10B is a flow chart illustrating a method for performing pass-thru communication.
Figure 10B:
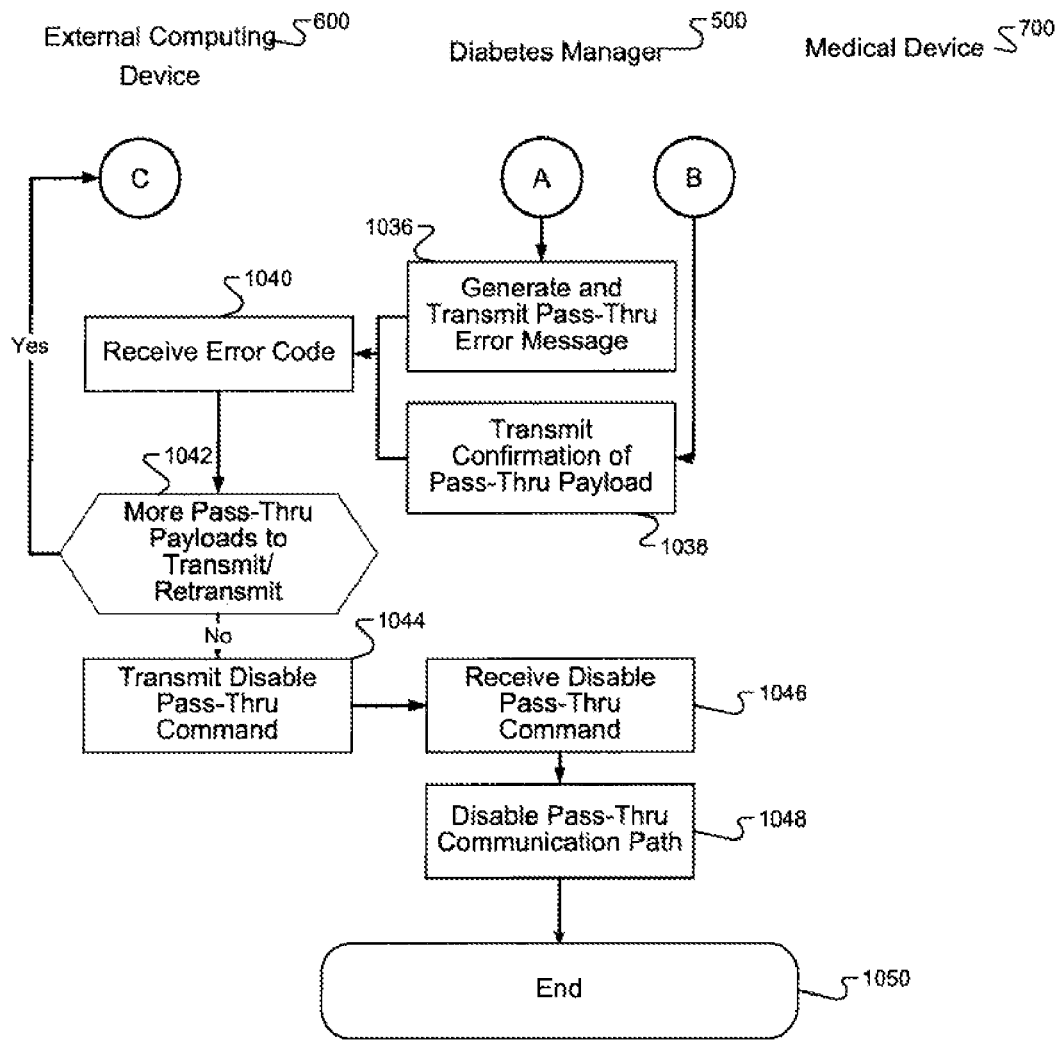

Referring now to FIGS. 10A and 10B, an exemplary method for performing pass-thru communication is depicted. It is appreciated that one or more of the commands described above can be used to effectuate pass-thru communication between an external computing device and a medical device. It is appreciated that communications between the external computing device 600 and the diabetes manager 500 are in accordance with the IEEE 11073 standard. Furthermore, in this example, the external computing device 600 communicates with the diabetes manager 500 over a wired bidirectional communication path, e.g. USB, and the medical device 700 communicates with the diabetes manager 500 over a wireless bidirectional communication path, e.g. Bluetooth.

Pass-thru communication can be initiated with an enable pass-thru command, as shown at step 1010. As discussed, the external computing device 600 transmits a command having a command/subcommand value, e.g. 0x8701, and a device identifier. Upon receiving the command, the diabetes manager 500 will parse the enable pass-thru command and determine which medical device to establish a pass-thru communication path with and attempts to establish a pass-thru communication path therewith, as shown at step 1012. Upon receiving the enable pass thru command, the diabetes manager 500 will confirm that communication is enabled with the selected medical device 700. In some embodiments, this can be achieved by sending a test communication or the like to the medical device 700. In other embodiments, a message indicating that pass-thru communication is enabled is sent to the medical device 700. In some embodiments, the medical device 700 will confirm that a communication path is established, as shown at step 1014. If the device does not exist or the communication path cannot be established, the diabetes manager 500 determines that the pass-thru communication path cannot be established, step 1016, and transmits an error response, e.g., RPC_ERR_APPLICATION_ERROR, to the external computing device 600. If a pass-thru communication path is determined to have been established, step 1016, the diabetes manager 500 transmits a response indicating that the pass-thru communication path has been established, step 1020, e.g. RPC_ERR_NO_ERRORS.

Once a pass-thru communication path has been established, pass-thru communication can commence, as shown at step 1022. The external computing device 600 will then send a pass-thru command to the diabetes manager. While the present example illustrates the external communication path transmitting pass-thru commands to the diabetes manager 500, it is appreciated that the medical device 700 can transmit pass-thru communication messages in a similar manner. It is appreciated that the steps following the transmission of a pass-thru command are substantially the same if sent from the medical device 700.

As discussed above, a pass-thru command includes the command/subcommand value of a pass-thru command, e.g. 0x8703, and the payload of the pass-thru message stored in a payload data array. Thus, the external computing device 600 will retrieve the data to be communicated to the medical device from a transmission buffer and will insert the data into the payload data array. The external computing device 600 will further format the pass-thru command as necessary, and may encrypt the command as well. Once the command is generated, the external computing device 600 will packetize the command in a first data packet having a first data packet structure which is suitable for transmission on the wired communication link. As discussed above, the first data packet will have a structure corresponding to communication protocol of the wired protocol, e.g. a USB packet. Once the pass-thru command is packetized and ready for transmission, the external computing device 600 will transmit the pass-thru command to the diabetes manager 500.

The diabetes manager 500 receives the data packet containing the pass-thru command. The diabetes manager 500 will then unpacketize the first data packet, step 1026, and will make sure that the command is not a disable pass-thru command (not shown). The diabetes manager 500 will then repacketize the pass-thru payload in a second data packet having a second data packet structure which is suitable for transmission on the wireless communication link, as shown at 1028. The foregoing steps can be achieved by parsing the first data packet to determine the payload data. The payload data will be in a predefined field in accordance with the communication protocol of the wired communication link. The diabetes manager will then generate the second data packet in accordance with the communication protocol of the wireless communication link, e.g. Bluetooth. The generated data packet will include the payload data received in the first data packet.

The diabetes manager 500 transmits the second data packet to the medical device 1030 over the wireless communication link. If the medical device 700 receives the second data packet, the medical device 700 transmits an acknowledgement to the diabetes manager 500, as shown at step 1030. The medical device 700 then executes the command contained in the payload, e.g. file I/O.

The diabetes manager 500 then determines if the transmission was successful and the pass-thru payload was received by the medical device 700, as shown at step 1034. If the transmission was not successful, the diabetes manager 500 will transmit a pass-thru error code, e.g. RPC_ERR_APPLICATION_ERROR, to the external computing device 600, as shown at 1036. If, however, the transmission was successful, the diabetes manager will generate and transmit an error code indicating a successful transmission, e.g. RPC_ERR_NO_ERRORS.

The external computing device receives the error code indicating an unsuccessful or successful transmission, as shown at step 1040. If the error code indicated an unsuccessful transmission or the transmission was successful and there are more payloads to transmit, the external computing device continues to generate pass-thru commands, e.g. returns to step 1024.

If the external computing device 600 and the medical device 700 are finished exchanging data, then the external computing device 600 will issue and transmit a disable pass-thru command. The disable pass-thru command includes a command/subcommand value, e.g. 0x8702. As was discussed earlier, the diabetes manager 500 checks each packet to ensure that the data packet does not contain a disable pass-thru command. Once the disable pass-thru command is received, step 1048, the diabetes manager 500 disables the pass-thru communication path.

The method shown above provides an example of a method that utilizes the commands for pass-thru communications described above. Furthermore, the foregoing method can further utilize commands such as the file I/O commands and firmware upgrade commands to effectuate actions such as reading a file from a medical device or upgrading the firmware of a medical device. The foregoing is not limiting and other methods may utilize the commands for pass-thru communications, file I/O, and firmware upgrades as well.

In view of the foregoing disclosure, diabetes management system has been disclosed. The diabetes management system configured to allow pass thru communication. The diabetes management system includes a diabetes management device, an external computing device that communicates with the diabetes management device over a first bidirectional communications link. The diabetes management device and the external computing device exchange first data packets of a first data packet structure over the first bidirectional communication link. The diabetes management system further includes a first medical device that performs a task related to diabetes management and that communicates with the diabetes management device over a second bidirectional communications link; wherein the diabetes management device and the first medical device exchange second data packets of a second data packet structure over the second bidirectional communication link. The diabetes management device includes a pass-thru module that:
v) selectively establishes a pass-thru communication path between the external computing device and the first medical device,
vi) receives first data packets of the first data packet structure from the external computing device via the first bidirectional communications link,
vii) converts the first data packets into second data packets of the second data packet structure, and
viii) transmits the second data packets to the first medical device over the second bidirectional communications link;

The pass-thru module uses a set of pass-thru commands for establishing a pass-thru communication path and enabling communication between the external computing device and the first medical device, and wherein the set of pass-through commands is defined in compliance with a communication protocol defined in accordance with IEEE standard 11073-20601.

In a further aspect of the disclosure, the diabetes management system further comprises a second medical device that performs a different task related to diabetes management and that communicates with the diabetes management device over a third bidirectional communications link. The diabetes management device and the second medical device exchange third data packets of a third data packet structure over the third bidirectional communication link. Furthermore the pass-thru module selectively establishes a second pass thru communication path between the external computing device and the second medical device.

In a further aspect of the disclosure, the set of pass-thru commands includes a enable pass-thru command for enabling pass-thru communication for one of the first medical device and the second medical device, wherein the command includes a device identifier that indicates which of the first medical device and the second medical device to enable pass thru communication with.

In a further aspect of the disclosure, the pass-thru module, in response to the enable pass-thru command received from the external computing device, establishes only one of the first communication path and the second communication path based on the device identifier in the enable pass-thru command.

In a further aspect of the disclosure, the set of pass-thru commands includes a transmit pass-thru payload command that instructs the diabetes management to transmit the first data packet payload from the external computing device to the first medical device, wherein the transmit pass-thru payload command includes a payload of the first data packet.

In a further aspect of the disclosure, the pass-thru module, in response to a transmit pass-thru payload command received from the external computing device, generates the second data packet by inserting the payload of the first data packet into the second data packet, and transmits the second data packet to the first medical device via the second communication link.

In a further aspect of the disclosure, the pass-thru module transmits a payload data event report to the external computing device when the second data packet is successfully transmitted to the first medical device and an error response when the second data packet is not successfully transmitted to the first medical device.

In a further aspect of the disclosure, the first communication link is a wired communication link and the second communication link is a wireless communication link.

In a further aspect of the disclosure, the first medical device is one of a durable insulin pump, a non-durable insulin pump, a continuous glucose monitor, and a mobile device.

In a further aspect of the disclosure, the pass-thru module is further configured to receive second data packets of the second data packet structure from the first medical device via the second bidirectional communications link, convert the second data packets into first data packets of the first data packet structure, and transmit the first data packets to the external computing device over the first bidirectional communications link.

Furthermore, a diabetes management device configured to provide an efficient pass-thru communication path between a first medical device and an external computing device has been described. The diabetes management device includes a first communications module configured to establish a first bidirectional communications link with the external computing device. The diabetes management device and the external computing device exchange first data packets of a first data packet structure over the first bidirectional communication link. The diabetes management device further includes a second communications module configured to establish a second bidirectional communications link with the first medical device. The diabetes management device and the first medical device exchange second data packets of a second data packet structure over the second bidirectional communication link. The diabetes management device further comprises a pass-thru module that:
v) selectively establishes a pass-thru communication path between the external computing device and the first medical device,
vi) receives first data packets of the first data packet structure from the external computing device via the first bidirectional communications link,
vii) converts the first data packets into second data packets of the second data packet structure, and
viii) transmits the second data packets to the first medical device over the second bidirectional communications link;

The pass-thru module uses a set of pass-thru commands for establishing a pass-thru communication path and enabling communication between the external computing device and the first medical device, and wherein the set of pass-through commands is defined in compliance with a communication protocol defined in accordance with IEEE standard 11073-20601.

While the foregoing has been described with respect to diabetes management systems, it is understood that the pass-thru communication commands can be used in other medical device systems. The IEEE 11073 standard extends to other medical devices and in view of the foregoing disclosure, the applicability of Applicant's private extension of the IEEE 11073 standard to other medical device systems should become apparent to one having skill in the art.

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

APPENDIX A

| Common RPC Numeric Object Attributes | | |
|---|---|---|
| Attribute Name | Value | Qualifier |
| Handle | The Handle attribute represents a reference ID for this object. Each object shall have a unique ID assigned by the agent. | M |
| Type | Defined in each of the numeric objects. | M |
| Metric-Spec-Small | mss-avail-intermittent \| mss-avail-stored-data \| mss-upd-aperiodic \| mss-msmt-aperiodic \| mssacc-agent-initiated \| mss-cat-manual. | M |

-continued

| Common RPC Numeric Object Attributes | | |
|---|---|---|
| Attribute Name | Value | Qualifier |
| Unit-Code | Defined in each of the numeric objects. | O |
| Attribute-Value-Map | Defined in each of the numeric objects | M |
| Absolute-Time-Stamp | AbsoluteTime as defined in ISO/IEEE 11073-20601 | M |
| Basic-Nu-Observed-Value | This attribute defines the numerical observed value of the object, without any further embedded status information, but with a smaller numerical representation compared to Simple-Nu-Observed-Value. One and only one of Simple-Nu-Observed-Value, Basic-Nu-Observed-Value or Nu-Observed-Value shall be present. | C |
| Simple-Nu-Observed-Value | This attribute defines the numerical observed value of the object, without any further embedded status information as found in Nu-Observed-Value. One and only one of Simple-Nu-Observed-Value, Basic-Nu-Observed-Value, or Nu-Observed-Value shall be present. | C |
| Nu-Observed-Value | This attribute defines the numerical observed value of the object and combines it with measurement status and unit information. It is used when status/unit are dynamic and are always provided together with the value. One and only one of Simple-Nu-Observed-Value, Basic-Nu-Observed-Value or Nu-Observed-Value shall be present. | |

APPENDIX B

Command Response Error Enumerations
  RPC_ERR_NO_ERRORS ::=0x0000
  RPC_ERR_CMD_CANCELLED ::=0x0001
  RPC_ERR_BLOCK_LENGTH ::=0x0002
  RPC_ERR_INVALID_PARAMETERS ::=0x0003
  Either the number of parameters or the content is not valid.
  RPC_ERR_INVALID_DATA ::=0x0004
  RPC_ERR_UNRECOGNIZED_CMD ::=0x0005
  RPC_ERR_UNRECOGNIZED_FEATURE:: =0x0006
  This error applies if the command is recognized, but the parameter is not.
  RPC_ERR_ABORTED_CMD ::=0x0007
  RPC_ERR_HARDWARE ::=0x0008
  Manager must invoke Read and Clear Status command to retrieve extended error information.
  RPC_ERR_APPLICATION ::=0x0009
  Manager must invoke Read and Clear Status command to retrieve extended error information.
  RPC_ERR_SECURITY_ERROR ::=0x000A
  This error indicates that a manager issued a command that does not exist for the currently authorized role, or that the digital signature check of a file fails.

What is claimed is:

1. A method for communicating between a computing device and a handheld medical device via an intermediary management device, comprising:
  receiving, by the intermediary management device, an enable pass-thru command from the computing device, where the computing device communicates over a first bidirectional communication link with the intermediary management device and the enable pass-thru command is defined as a private extension of IEEE standard 11073-20601;

establishing, by the intermediary management device, a pass-thru communication path from the computing device to the handheld medical device, where the pass-thru communication path is established in response to the enable pass-thru command;

receiving, by the intermediary management device, a data packet via the first bidirectional communication link from the computing device, where the data packet has a first packet structure and is received subsequent to the enable pass-thru command;

converting, by the intermediary management device, the data packet from the first packet structure to a second packet structure; and transmitting, by the intermediary management device, the converted data packet over a second bidirectional communication link to the handheld medical device.

2. The method of claim 1 further comprises establishing the pass-thru communication path with the handheld medical device in accordance with a device identifier, wherein the device identifier corresponds to the handheld medical device and is included in the enable pass-thru command.

3. The method of claim 1 wherein receiving a data packet from the computing device further comprises receiving a transmit pass-thru payload command from the computing device, where the transmit pass-thru payload command includes a payload of the data packet and is defined as a private extension of IEEE standard 11073-20601.

4. The method of claim 3 further comprises converting the data packet from the first packet structure to the second packet structure in response to the transmit pass-thru payload command.

5. The method of claim 1 further comprises receiving, by the intermediary management device, a data packet from a third device that differs from the computing device and transmitting an error code back to the third device while the pass-thru communication path is established between the computing device and the intermediary management device.

6. The method of claim 1 further comprises receiving, by the intermediary management device, a receipt confirmation message from the handheld medical device and transmitting, by the intermediary management device, a transmission report over the first bidirectional communication link to the computing device, the transmission of the transmission report in response to receiving the receipt confirmation message.

7. The method of claim 1 further comprises receiving, by the intermediary management device, a disable pass-thru command and disabling the pass-thru communication path in response to the disable pass-thru command.

8. The method of claim 1 further comprises
receiving, by the intermediary management device, a data packet via the second bidirectional communication link from the handheld medical device, where the data packet has the second packet structure;
converting, by the intermediary management device, the data packet from the second packet structure to the first packet structure; and
transmitting, by the intermediary management device, the converted data packet over the first bidirectional communication link to the computing device.

9. The method of claim 1 wherein the handheld medical device is further defined as one of a blood glucose monitor and an insulin pump.

10. A method for communicating between a computing device and a handheld medical device via an intermediary management device, comprising:
establishing, by the intermediary management device, a pass-thru communication path from the computing device to the handheld medical device, where the computing device communicates over a first bidirectional communication link with the intermediary management device;

receiving, by the intermediary management device, a transmit pass-thru payload command via the first bidirectional communication link from the computing device, where the transmit pass-thru payload command includes a payload from one or more data packets having a first packet structure and is defined as a private extension of IEEE standard 11073-20601 and the transmit pass-thru payload command is received subsequent to the enable pass-thru command;

converting, by the intermediary management device, the payload from the first packet structure to a second packet structure; and transmitting, by the intermediary management device, the converted payload over a second bidirectional communication link to the handheld medical device.

11. The method of claim 10 further comprises receiving, by the intermediary management device, an enable pass-thru command from the computing device, where the enable pass-thru command is defined as a private extension of IEEE standard 11073-20601.

12. The method of claim 10 further comprises converting, by the intermediary management device, the payload from the first packet structure to the second packet structure in response to the transmit pass-thru payload command.

13. The method of claim 10 further comprises receiving, by the intermediary management device, a data packet from a third device that differs from the computing device and transmitting an error code back to the third device while the pass-thru communication path is established between the computing device and the intermediary management device.

14. The method of claim 10 further comprises receiving, by the intermediary management device, a receipt confirmation message from the handheld medical device and transmitting, by the intermediary management device, a transmission report over the first bidirectional communication link to the computing device, the transmission of the transmission report in response to receiving the receipt confirmation message.

15. The method of claim 10 further comprises receiving, by the intermediary management device, a disable pass-thru command and disabling the pass-thru communication path in response to the disable pass-thru command.

16. The method of claim 10 further comprises
receiving, by the intermediary management device, a data packet via the second bidirectional communication link from the handheld medical device, where the data packet has the second packet structure;
converting, by the intermediary management device, the data packet from the second packet structure to the first packet structure; and
transmitting, by the intermediary management device, the converted data packet over the first bidirectional communication link to the computing device.

17. The method of claim 10 wherein the handheld medical device is further defined as one of a blood glucose monitor and an insulin pump.

18. A method for communicating between a computing device and a handheld medical device via an intermediary management device, comprising:
receiving, by the intermediary management device, an enable pass-thru command from the computing device, where the computing device communicates over a first bidirectional communication link with the intermediary management device and the enable pass-thru command is defined as a private extension of standardized communication protocol;

establishing, by the intermediary management device, a pass-thru communication path from the computing device to the handheld medical device, where the pass-thru communication path is established in response to the enable pass-thru command;

receiving, by the intermediary management device, a transmit pass-thru payload command via the first bidirectional communication link from the computing device, where the transmit pass-thru payload command includes payload of a data packet having a first packet structure and is defined as a private extension of standardized communication protocol and the transmit pass-thru payload command is received subsequent to the enable pass-thru command;

converting, by the intermediary management device, the data packet from the first packet structure to a second packet structure; and transmitting, by the intermediary management device, the converted data packet over a second bidirectional communication link to the handheld medical device.

19. The method of claim 18 further comprises establishing the pass-thru communication path with the handheld medical device in accordance with a device identifier, wherein the device identifier corresponds to the handheld medical device and is included in the enable pass-thru command.

\* \* \* \* \*